United States Patent
Evans et al.

(10) Patent No.: US 8,323,909 B2
(45) Date of Patent: Dec. 4, 2012

(54) METHODS OF IDENTIFYING SMALL MOLECULES FOR RENEWALS, SURVIVAL AND MIGRATION OF CARDIAC PROGENITORS

(75) Inventors: Sylvia Evans, Del Mar, CA (US); Ju Chen, San Diego, CA (US); Lizhu Lin, La Jolla, CA (US); Ken Chien, La Jolla, CA (US); Yibing Qyang, San Diego, CA (US); Alessandra Moretti, La Jolla, CA (US); Karl Laugwitz, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 172 days.

(21) Appl. No.: 12/770,597

(22) Filed: Apr. 29, 2010

(65) Prior Publication Data

US 2010/0261196 A1 Oct. 14, 2010

Related U.S. Application Data

(63) Continuation of application No. 11/799,839, filed on May 2, 2007, now abandoned, which is a continuation-in-part of application No. 10/544,053, filed on Apr. 13, 2006, now Pat. No. 7,745,113.

(60) Provisional application No. 60/797,338, filed on May 2, 2006.

(51) Int. Cl.
*C12N 5/00* (2006.01)
*G01N 33/53* (2006.01)

(52) U.S. Cl. .................. 435/7.1; 435/375; 435/377

(58) Field of Classification Search ............... None
See application file for complete search history.

(56) References Cited

FOREIGN PATENT DOCUMENTS

WO WO 02/12498 A2 2/2002

OTHER PUBLICATIONS

Laugwitz et al. (Nature. 2005; 433:647-653).*
Soriano (Nature Genetics. 1999; 21:70-71).*
Cai et al (Developmental Cell. 2003; 5: 877-889).*
Ahlgren et al., "Independent requirement for ISL1 in formation of pancreatic mesenchyme and islet cells", *Nature.*, 385(6613):257-260 (1997).
Amit et al., "Clonally derived human embryonic stem cell lines maintain pluripotency and proliferative potential for prolonged periods of culture", *Dev. Biol.*, 227(2):271-278 (2000).
Boheler et al., "Differentiation of pluripotent embryonic stem cells into cardiomyocytes", *Circ. Res.*, 91(3):189-201 (2002).
Boyer et al., "Core transcriptional regulatory circuitry in human embryonic stem cells", *Cell.*, 122(6):947-956 (2005).
Cai et al., "Isl1 identifies a cardiac progenitor population that proliferates prior to differentiation and contributes a majority of cells to the heart", Dev. Cell., 5(6):877-889 (2003).
Ericson et al., "Early stages of motor neuron differentiation revealed by expression of homeobox gene Islet-1", *Science.*, 256(5063):1555-1560 (1992).
Hamburger and Hamilton, "A Series of Normal Stages in the Development of the Chick Embryo", *J. Morphol.*, 88: 49-92 (1951).
Pfaff et al., "Requirement for LIM homeobox gene Isl1 in motor neuron generation reveals a motor neuron-dependent step in interneuron differentiation", Cell., 84(2):309-320 (1996).
Schilling et al., "Regulation of left-right asymmetries in the zebrafish by Shh and BMP4", *Dev. Biol.*, 210(2):277-287 (1999).
Stenman et al., "Identification of two distinct progenitor populations in the lateral ganglionic eminence: implications for striatal and olfactory bulb neurogenesis", J. Neurosci., 23(1):167-74 (2003).
Yuan and Schoenwolf, "Islet-1 marks the early heart rudiments and is asymmetrically expressed during early rotation of the foregut in the chick embryo", Anat. Rec., 260(2):204-207 (2000).

* cited by examiner

*Primary Examiner* — Scott Long
(74) *Attorney, Agent, or Firm* — DLA Piper LLP (US)

(57) ABSTRACT

The present invention relates to a small molecule high-throughput screening assay consisting of detectably labeled cardiac progenitor cells. The invention also describes a method of identifying small molecules from the high-throughput assay affecting cardiogenesis and/or modulating cardiac progenitor cell development. Also described are methods of stimulating maturation of cardiac progenitor cells using a GSK-3β inhibitor.

6 Claims, 15 Drawing Sheets

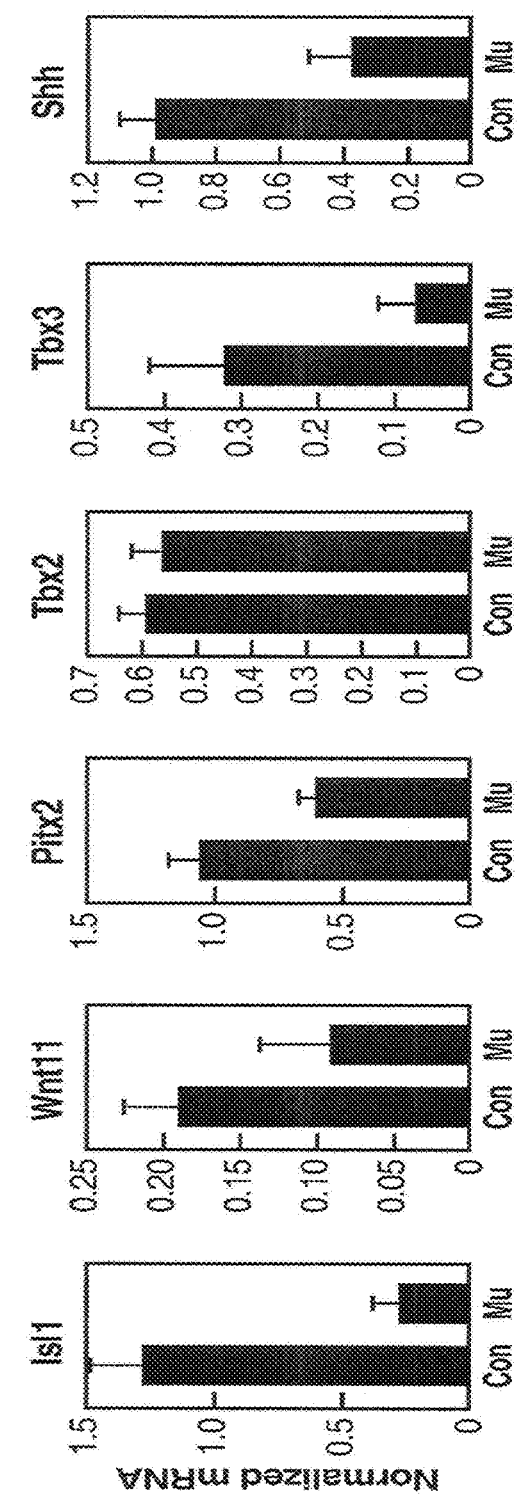

METHODS OF IDENTIFYING SMALL MOLECULES FOR RENEWALS, SURVIVAL AND MIGRATION OF CARDIAC PROGENITORS

CROSS REFERENCE TO RELATED APPLICATIONS

This application is a continuation application of U.S. application Ser. No. 11/799,839, filed May 2, 2007, now pending, which is a continuation-in-part under 35 U.S.C. §120 of U.S. application Ser. No. 10/544,053, filed Apr. 13, 2006, now pending, and claims the benefit of priority under 35 U.S.C. §119(e) of U.S. Ser. No. 60/797,338, filed May 2, 2006. The disclosure of each of the prior applications is considered part of and is incorporated by reference in the disclosure of this application.

GRANT INFORMATION

This invention was made with government support under Grant No. HL074066 awarded by the National Institutes of Health. The government has certain rights in the invention.

FIELD OF THE INVENTION

The present invention relates generally to a high-throughput screening assay and more specifically to a method of identifying small molecules affecting cardiac progenitor cells.

BACKGROUND INFORMATION

The heart is composed of diverse muscle and non-muscle cell lineages: atrial/ventricular cardiac myocytes, conduction system cells of the working myocardium, smooth muscle/endothelial cells of the coronary arteries and veins, endocardial cells, valvular components and connective tissue. Congenital heart diseases can arise from defects in the pathways for heart lineage specification, and human degenerative diseases can arise in a subset of ventricular and pacemaker cell lineages. The pathways that guide heart cell lineage diversification are relatively obscure, as the primordial heart precursor cells have not been clearly identified.

Recent work has defined two fields of cardiac progenitors, dubbed the primary and secondary, or anterior heart fields. The primary heart field is believed to give rise to the atria and ventricles of the heart, while the secondary or anterior field is believed to give rise to the outflow tract. The secondary field is believed to reside anterior and dorsal to the heart at the early linear heart tube stage. Initial evidence that the outflow tract of the heart was not present in the linear heart tube came from a series of in vivo lineage studies performed in chick embryos. These studies demonstrated that the outflow tract was not present at the linear heart tube stage, but did not indicate where the outflow tract came from at a later stage.

Recently, the source of the outflow tract has been addressed by studies in chick and mouse embryos. Results of these studies demonstrated that some cells in the outflow tract originate from splanchnic mesoderm adjacent to the pharyngeal endoderm. The extent of the contribution, and the boundaries of the "secondary" or "anterior" heart field could not be definitively assessed from results of these experiments.

Several studies have demonstrated induction of cardiogenic mesoderm in response to inhibition of Wnt signaling in chick, *Xenopus* and mouse embryos. Wnt antagonists Dickkopf1 and Crescent produced by anterior endoderm in chick embryos stimulate differentiation of cardiogenic mesoderm. In frog embryos, Dkk1 and Crescent secreted by Spemann's organizer are also initiators of cardiac differentiation, acting indirectly on anterior mesendoderm to provoke secretion of an as yet unidentified cardiogenic induction factor. In mouse embryos, ablation of β-catenin utilizing a Cytokeratin19 promoter-driven Cre (K19-Cre) recombinase resulted in ectopic heart formation, which was attributed to ablation of β-catenin in endodermal tissues.

In contrast to the foregoing, activation of Wnt signaling is required for cardiogenesis in *Drosophila*, and in cell culture systems, including embryonic stem cells, and embryonal carcinoma P19 cells. In these cell culture systems, however, the spatial requirement for Wnt signaling has not been addressed.

SUMMARY OF THE INVENTION

Islet1 is the only gene known to date that is specifically expressed in cardiogenic stem cells, but not in differentiated cardiac cells. Islet1 may be a master regulator of the cardiogenic stem cell state. This discovery enables use of islet1 expression as a means to isolate endogenous cardiogenic stem cells, or to create cardiogenic stem cells.

The present invention relates to a detectably labeled screening assay including injecting tamoxifen into a transgenic non-human animal having a tamoxifen-dependent Cre-recombinase in the isl1 locus (isl1-mER-Cre-mER) and a Cre reporter (R26R), and isolating at least one cell fraction, wherein the cells express beta-galactosidase, thereby creating a detectably labeled screening assay.

The present invention also relates to a method of identifying a detectably labeled small molecule which modulates cardiac progenitor cells by labeling a cell fraction isolated from a transgenic non-human animal having a tamoxifen-dependent Cre-recombinase in the isl1 locus (isl1-mER-Cre-mER) and an Cre reporter (R26R) with a fluorescent label, wherein the cell fraction contains detectably labeled cardiac progenitor cells, identifying a test molecule from the cell fraction which has increased fluorescence as compared to a control molecule, contacting the test molecule with the detectably labeled cardiac progenitor cells, and determining the expression of the isl1+ transcription factor. Molecules identified by this method include those molecules identified in FIG. 5, e.g., 6-bromoindirubin-3'-oxime (BIO).

The present invention also relates to identifying small molecules which regulate cardiac progenitor cells by labeling a cell fraction isolated from a transgenic non-human animal having a tamoxifen-dependent Cre-recombinase in the isl1 locus (isl1-mER-Cre-mER) and an Cre reporter (R26R) with a fluorescent label, wherein the cell fraction contains detectably labeled cardiac progenitor cells, identifying a test molecule from the cell fraction which has increased fluorescence as compared to a control molecule, contacting the test molecule with the detectably labeled cardiac progenitor cells, determining the expression of the isl1+ transcription factor, and identifying a factor which is affected by isl1+ expression.

The present invention also relates to stimulating maturation of cardiac progenitor cells by contacting the cells with an effective amount of a GSK-3β inhibitor, such as BIO.

Also provided is a method for generating an Isl1 lineage-traced cell by contacting an undifferentiated progenitor cell that expresses Isl1 with a GSK-3β inhibitor, such as BIO, that activates or enhances expression of Isl1 in the cell. In one embodiment, the cell differentiates into a cardiomyocyte, endothelial cell, or smooth muscle cell. Other markers may also be incorporated, including, but not limited to, insertion of lacZ or fluorescent marker genes into the endogenous Islet1 locus, contained within the genomic, or within a BAC, or within other kinds of transgenes, for example utilizing an islet1 promoter fragment to drive expression of a reporter gene.

In another embodiment, the undifferentiated progenitor cell is an embryonic or post-natal heart muscle cell that is derived from a rat, mouse or human, for example. Other sources for islet progenitors include, but are not limited to, embryonic stem cells, progenitors from cord blood, and other adult progenitor cells, including, but not limited to, those from bone marrow, or adipose tissue. In another embodiment, islet1 protein may be detected by antibody staining, thereby identifying cardiac progenitors. Other markers may be identified on the basis of islet1 presence, and may be utilized for screening in a similar manner to that described above.

BRIEF DESCRIPTION OF THE DRAWINGS

FIGS. 10A-10F are graphical diagrams showing analysis of potential downstream effector targets in Isl1-Cre; β-catenin mutants and control littermates. Results from Real-Time qPCR analyses. Within FIGS. 10A-10F, the following abbreviations mean: Con, Isl1-Cre/+, β-catenin+/f; Mu, Isl1-Cre/+; β-catenin/f.

As shown in FIG. 12A, the mouse (SEQ ID NO: 11) and human (SEQ ID NO: 12) Isl1 5'-promoters are provided with conserved LEF1 binding sites.

DETAILED DESCRIPTION OF THE INVENTION

Figure 1:
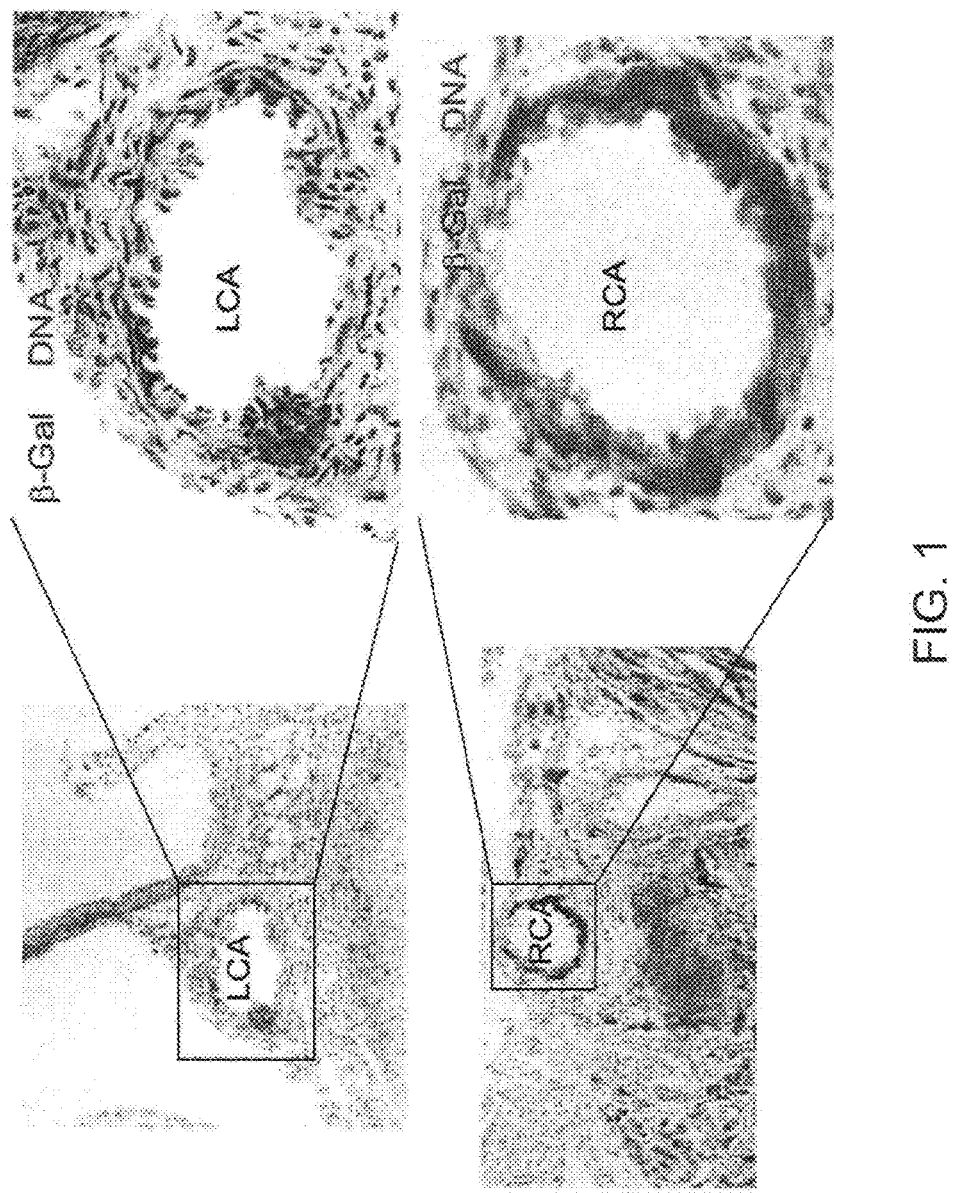
FIG. 1 is a pictorial diagram showing a genetic marking of isl1+ progenitors and vascular cell fate. Shown are cross sections of the right and left coronary artery of isl1-IRES-Cre/R26R double heterozygous hearts. β-gal expression can localized throughout the whole wall of both coronary arteries.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The terms "sample" and "biological sample" as used herein, refer to any sample suitable for the methods provided by the present invention. In one embodiment, the biological sample of the present invention is a tissue sample, e.g., a biopsy specimen such as samples from needle biopsy. In other embodiments, the biological sample of the present invention is a sample of bodily fluid, e.g., serum, plasma, urine, and ejaculate.

The term "population of cells" or "library of cells" as used herein, refers to at least two cells, at least about $10^3$ cells, at least about $10^4$ cells, and at least about $10^5$ to $10^9$ cells. The population or sample can contain a mixture of different cell types from either primary or secondary cultures although samples containing only a single cell type are desirable, for example, a cardiogenic progenitor cell population.

The term "therapeutically effective amount" or "effective amount" means the amount of a compound or pharmaceutical composition that will elicit the biological or medical response of a tissue, system, animal or human that is being sought by the researcher, veterinarian, medical doctor or other clinician.

Stem cells have been defined in many different ways. However, the main principles include: (1) self-renewal, or the ability to generate daughter cells with characteristics similar to the initiating mother cell; (2) multi-lineage differentiation of a single cell; and (3) in vivo functional reconstitution of damaged tissue. As such, an Islet1 progenitor may be a bona fide stem cell, or a pluripotential progenitor cell, which is marked by Islet1.

Embryonic Stem (ES) cells, first obtained from mouse and more recently from non-human primates and human blastocysts, display all three characteristics. ES cells are pluripotent cells derived from the inner cell mass of the blastocyst that can be propagated indefinitely in an undifferentiated state. Both mouse and human ES cell-lines have been maintained continuously in culture for more than 300 cell doublings. ES cells differentiate into all somatic cell types when injected into a blastocyst and form mature progeny cells of all three embryonic germ layers in vitro. Finally, all differentiated progeny of ES cells are functional cells, as mice generated by tetraploid embryo complementation are viable. Although ES cells have been isolated from humans, their use in research as well as their therapeutic potential is encumbered by ethical considerations.

Most adult stem cells also fulfil the stem cell criteria mentioned above, even though the degree of self-renewal and differentiation is less than that seen for ES cells. The best studied adult stem cell, the hematopoietic stem cell (HSC), undergoes in vivo self-renewing cell divisions, differentiates at the single cell level into all mature blood elements, and functionally repopulates the bone marrow of myeloablated animals and humans. Other adult stem cells have been more recently defined and are, therefore, less well studied. However, neural stem cells (NSC), mesenchymal stem cells (MSC) and epidermal stem cells all fulfil these basic criteria. Other cells also termed stem cells, such as angioblasts or endothelial stem cells, display all the required characteristics, except that they differentiate only into a single type of cells.

The term "progenitor cell" as used herein, refers to any somatic cell which has the capacity to generate fully differentiated, functional progeny by differentiation and proliferation. "Differentiation" refers to a change that occurs in cells to cause those cells to assume certain specialized functions and to lose the ability to change into certain other specialized functional units. Cells capable of differentiation may be any of totipotent, pluripotent or multipotent cells. Differentiation may be partial or complete with respect to mature adult cells.

Progenitor cells include progenitors from any tissue or organ system, including, but not limited to, blood, nerve, muscle, skin, gut, bone, kidney, liver, pancreas, thymus, and the like. Progenitor cells are distinguished from "differentiated cells," which are defined as those cells which may or may not have the capacity to proliferate, i.e., self-replicate, but which are unable to undergo further differentiation to a different cell type under normal physiological conditions. Moreover, progenitor cells are further distinguished from abnormal cells such as cancer cells, especially leukemia cells, which proliferate (self-replicate) but which generally do not further differentiate, despite appearing to be immature or undifferentiated.

Progenitor cells include all the cells in a lineage of differentiation and proliferation prior to the most differentiated or the fully mature cell. An uncommitted progenitor can be described as being "totipotent," i.e., both necessary and sufficient for generating all types of mature blood cells. Progenitor cells which retain a capacity to generate all blood cell lineages but which can not self-renew are termed "pluripotent." Cells which can produce some but not all blood lineages and can not self-renew are termed "multipotent."

As such, "totipotent cell" and "totipotent stem cell" are used interchangeably throughout and refer to a stem cell that has the capacity to become any type of cell in a mammalian body. "Pluripotent" and "multipotent" are used interchangeably throughout and refer to a stage where a cell can still become one of a plurality of cells but can no longer become any type of cell in the body. Accordingly, "pluripotent" cells are not referred to as "stem cells" but rather "progenitor cells" because they are progenitors to one or more type of a plurality of cells. The stems cells may be embryonic stem cells or bone marrow stem cells.

It has been discovered that Islet1 is a transcription factor that is a unique marker for proliferating cardiac stem cells. Previous studies have demonstrated a key role for the LIM homeodomain transcription factor Islet1 (Isl1) in cardiac development, and as a marker for pluripotent cardiovascular progenitors which give rise to cardiomyocyte, endothelial and smooth muscle lineages in vitro. Isl1 marks proliferating, undifferentiated progenitors of the second heart field which are located dorsal/medially to the heart. Thus, Isl1 appears to be required for proliferation, survival, and migration of these progenitors into the forming heart. The second heart field migrates in and differentiates later than progenitors of the first heart field. Expression is downregulated in second heart lineages as differentiation occurs. The second heart lineage includes cells of the secondary or anterior heart field which will give rise to the outflow tract, or outflow tract and right ventricle, respectively. Mice which are null for Isl1 die embryonically at E10 with hearts missing segments derived from the second heart field, including the outflow tract, right ventricle, and exhibiting severely reduced atrial tissue.

Islet1 is the only gene known to date that is specifically expressed in cardiogenic stem cells, but not in differentiated cardiac cells. Islet1 may be a master regulator of the cardiogenic stem cell state. This discovery enables use of islet1 expression as a means to isolate endogenous cardiogenic stem cells, or to create cardiogenic stem cells. Islet1 is also expressed in other progenitor, or "stem cell" populations, including those of the pancreas, the neural crest, the aorta-gonad-mesonephros region (hematopoietic and endothelial progenitors), the allantois, and other cell types. This expression, in concert with data described herein pertaining to cardiogenic stem cells, shows that islet marks, not only cardiogenic stem cells, but other pluripotent stem cells as well.

Islet1 is a unique identifier of this cell population. Islet1 is also required for these precursors to contribute to development of the heart. In islet1 mutants, cardiogenic lineages normally derived from islet1-expressing progenitors are absent. Thus, Islet is unique in being expressed in a number of embryonically distinct pluripotential progenitors. Islet is a transcription factor that drives the stem cell state.

Utilizing islet1 as a marker, cells can be isolated from early embryos, hybridized with fluorescently labeled islet1 antibodies, and sorted for stem cells by FACS. Isl1 also marks cardiac progenitors found within postnatal heart of rodents and humans. These progenitors can be isolated, propagated, and readily differentiate into functional cardiomyocytes when co-cultured with neonatal cardiac myocytes. Alternatively, genes (e.g., lacZ, GFP, cre) can be inserted into the endogenous islet1 locus and used as a basis of cell identification or sorting. Cardiogenic stem cell lines can be created by expressing islet1 alone or in combination with Nkx2.5, another transcription factor that is expressed in cardiac progenitors, but is also expressed in differentiated cardiac cells. To differentiate these cardiogenic precursors, islet1 expression was down regulated by genetic means or by application of growth factors. Other stem cell lines can be created in a similar manner, expressing islet1 alone or in combination with other factors specific to distinct lineages, to create pluripotent cells, which can differentiate to multiple lineages, or specific lineages dependent on the genetic or physical environment.

The severe cardiac phenotype of isl1$^{-/-}$ mice led to investigation of expression of isl1 during early stages of mouse heart development. Single and double whole mount in situ hybridization was performed on embryos from ED7.25 to ED 8.75, utilizing probes for isl1 and MLC2a mRNAs. The latter is one of the earliest markers for differentiated cardiogenic precursors. Results of this whole mount in situ and subsequent section analysis demonstrated that islet1 is never co-expressed with MLC2a, but rather is expressed in an immediately adjacent population of cells. At the early cardiogenic crescent stages, islet1 expressing cells are medial and dorsal to MLC2a expressing cells. As the heart tube forms, islet1 positive cells within splanchnic mesenchyme comprising the mesocardium and adjacent to foregut endoderm are contiguous with MLC2a positive cells throughout their extent, including anterior and posterior regions. Islet1 is expressed in both splanchnic mesoderm and in ventral foregut endoderm.

More recent studies have demonstrated that Isl1 marks a pluripotential cardiovascular cell which co-expresses flk1 and Nkx2.5, that can be cloned and amplified from either embryonic stem cells or embryos. Amplified clones can give rise to endothelial, smooth muscle, and cardiomyocyte cell types. The pivotal role for Isl1 within cardiovascular progenitors makes it critical to understand factors which regulate Isl1 expression in this context. Although islet1 was not expressed in differentiating MLC2a positive myocardial precursors, it was expressed in the region of the recently identified secondary or anterior heart field, that is, splanchnic mesodermal cells of the pharyngeal region. Recent evidence has indicated that the anterior heart field in mouse contributes to the outflow tract. This observation, in concert with the cardiac phenotype in islet1 mutants, indicated that islet1 expressing cells might contribute to the outflow tract of the heart.

To investigate this question, lineage analysis of isl1 expressing cells was performed, by crossing an islet1-cre mouse with the Rosa26-lacZ indicator mouse. In progeny of this cross, Cre-mediated excision brings the lacZ gene under the control of the ubiquitously expressed *Rosa26* locus, enabling the fate of isl1 expressing cells to be followed by staining for β-galactosidase activity, even when transcription from the endogenous isl1 locus has been repressed. Results of this analysis were startling, and demonstrated that cells which previously expressed islet1 make a substantial contribution to the embryonic heart, comprising a majority of cells in the outflow tract, right ventricle, and atria, and also contribute to specific regions of the left ventricle. The β-galactosidase positive cells were also observed within the endocardium, and within endothelial cells lining the aortic arch arteries. The majority of β-galactosidase negative myocardial cells were observed within the ventral aspect of the left ventricle and the anterior ventral region of the left atria.

The observation that islet1-expressing cells contribute a majority of cells to the developing heart was consistent with the inventors' previous analysis of the cardiac phenotype in isl1 homozygous mutant mice, where whole segments of the heart were missing. The missing structures indicated that Islet1 might be required for proliferation, survival and/or migration of islet1 expressing cardiogenic precursors. To address this question, an attempt was made to examine isl1 expressing cells within isl1 mutants and littermate controls. Although targeting of the isl1 gene deleted the third exon, containing the second LIM domain, the 5' end of isl1 mRNA is still expressed in the mutant, enabling detection of islet1 message in mutant cells. Islet protein, however, is not detectable (Pfaff et al., 1996).

To track isl1 expressing cells in mutant and wild type embryos, whole mount in situ hybridization analysis was performed on embryos from ED8.5-ED10 with a probe for isl1 mRNA. Results of this analysis demonstrated that there are progressively fewer islet-expressing cells in the mutant, although some cells still remain. In conjunction with the cardiac phenotype of isl1 mutants, these results indicate that Islet is required for cell proliferation and/or cell survival.

The results of these studies show that Islet1 is required for cell proliferation and survival of cardiogenic precursors, and that downstream targets of Islet1 are mediating this effect. Two growth factor pathways which have been implicated in growth and survival of cardiogenic precursors in both vertebrate and invertebrate heart development are bone morphogenetic proteins (BMPs), and fibroblast growth factors (FGFs). A number of BMPs and FGFs have been described as being expressed in embryonic regions that overlap with and/or are adjacent to islet1-expressing cells, including BMPs 2, 4, 6 and 7, and FGFs 4, 8, and 10. To determine if any of these are targets of Islet1 action, whole mount in situ hybridization was performed with probes for these growth factor genes. Results of this analysis demonstrated a decrease in expression in each of these genes in isl1 null mice. Expression of some of these growth factors was severely down regulated or undetectable in regions that overlapped islet1 expression, including expression of BMP4, BMP7, and FGF10. These genes are likely to be direct or indirect targets of Islet. Expression of the other BMP and FGF genes was still present, but the domain of expression was decreased in regions overlapping with islet1 expression, similar to results observed with islet 1 mRNA in islet1 mutants. This decrease may reflect a decrease in the number of cells that express these growth factors.

As such, in one embodiment of the invention, there is provided a screening assay which includes injecting tamoxifen into a transgenic non-human animal having a tamoxifen-dependent Cre-recombinase in the isl1 locus (isl1-mER-Cre-mER) and a Cre reporter (R26R), and isolating at least one cell fraction, wherein the cells express a detectable marker, e.g., .beta.-galactosidase, thereby creating a detectably labeled screening assay. In another embodiment, the screening assay may be performed on embryonic stem cells engineered to express .beta.-galactosidase under the control of the endogenous islet1 promoter.

Figure 5:
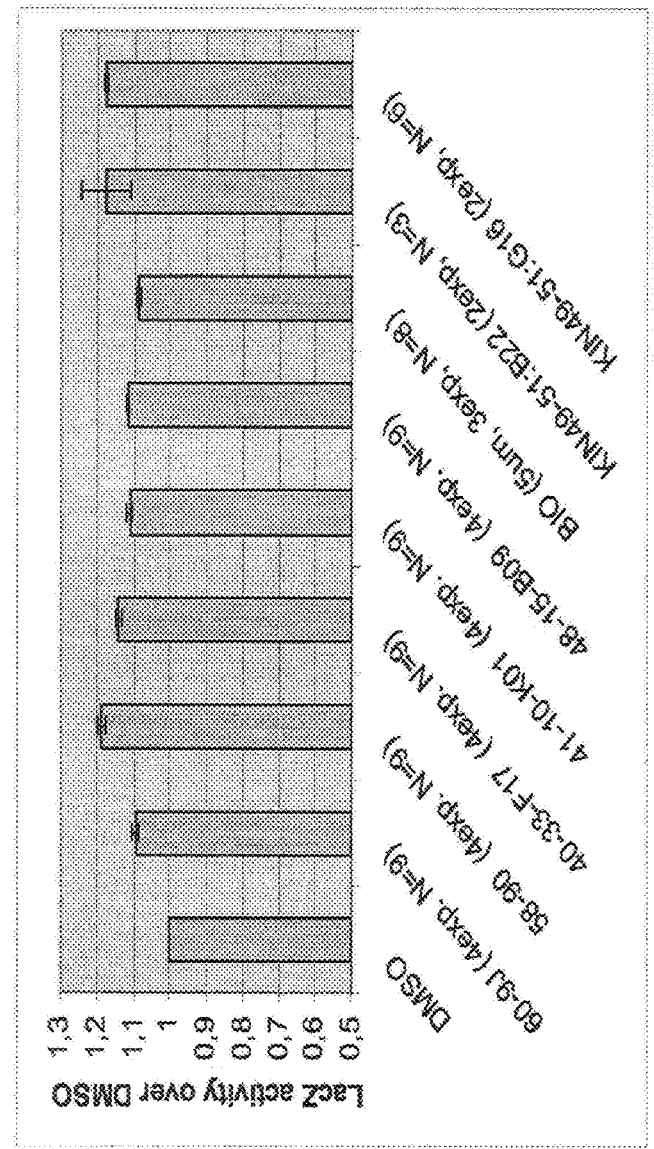
FIG. 5 is graphical diagram showing a summary of chemical compounds which reached a significant increase of β-galactosidase activity after 4 days in culture in the cardiac progenitor cells. The GSK-3β inhibitor BIO showed a significant increase in β-galactosidase activity, β-gal$^+$ progenitor cell number and proliferation of isl1$^+$ precursor cells in the above described assay system.

Still, in another embodiment of the invention, there is provided a method of identifying a detectably labeled small molecule which modulates cardiac progenitor cells by labeling a cell fraction isolated from a transgenic non-human animal having a tamoxifen-dependent Cre-recombinase in the isl1 locus (isl1-mER-Cre-mER) and an Cre reporter (R26R) with a fluorescent label, wherein the cell fraction contains detectably labeled cardiac progenitor cells, identifying a test molecule from the cell fraction which has increased fluorescence as compared to a control molecule, contacting the test molecule with the detectably labeled cardiac progenitor cells, and determining the expression of the isl1+ transcription factor. Molecules identified by this method include those molecules identified in FIG. 5, e.g., BID (Meijer et al., Chem. Biol. 10(12):1255, 2003).

The present invention also provides a method of identifying small molecules which regulate cardiac progenitor cells by labeling a cell fraction isolated from a transgenic non-human animal having a tamoxifen-dependent Cre-recombinase in the isl1 locus (isl1-mER-Cre-mER) and an Cre reporter (R26R) with a fluorescent label, wherein the cell fraction contains detectably labeled cardiac progenitor cells, identifying a test molecule from the cell fraction which has increased fluorescence as compared to a control molecule, contacting the test molecule with the detectably labeled cardiac progenitor cells, determining the expression of the isl1+ transcription factor, and identifying a factor which is affected by isl1+ expression.

One aspect of the invention described herein is the ability to screen large numbers of small compounds utilizing Islet1 to identify various small molecules and associated factors which regulate and modulate cardiogenesis. A stem cell is a progenitor cell which can proliferate and give rise to a number of distinct lineages. Islet1-expressing cells conform to this definition, giving rise to a number of distinct cardiac lineages. The unique property of islet1 in being expressed in cells prior to differentiation should allow for cell sorting on the basis of islet1 expression. Additionally, Islet1's role in dictating the proliferation and/or survival of these cells indicates that Islet1, in concert with other factors, may be utilized to drive a cardiogenic stem cell state.

Thus, the present invention also provides a method of stimulating maturation of cardiac progenitor cells by contacting the cells with an effective amount of a GSK-30 inhibitor. Likewise, the invention provides a method for generating an Isl1 lineage-traced cell by contacting an undifferentiated progenitor cells that expresses Isl1 with a GSK-3β inhibitor.

Based on the considerations outlined above, a high-through-put screening assay is provided which allows for identification of various small molecules affecting cardiogenesis or affecting the development of cardiac progenitor cells.

For example, the requirement that cardiac progenitor cells require a feeder layer or a conditioned medium from cardiac fibroblasts indicates that the cells provide small molecules and/or factors that suppress the differentiation or promote the self-renewal of the and development of multipotent progenitor cells. An activity with these properties is referred to as differentiation-inhibiting activity of i-cells (DIAI). For murine ES cells, leukaemia inhibitory factor (LIF), a member of the cytokine family related to interleukin-6, can replace the requirement for feeder cells. For inhibiting murine ES cell differentiation activation of the signaling component of the LIF receptor, glycoprotein 130 (gp 130), is both necessary and sufficient. However, human ES cells and cardiac i-cells do not seem to require LIF for blocking differentiation and stimulating self-renewal.

Until now, no in vitro culture conditions have been established that allow identification of molecules in vivo. The high-throughput screening assay described herein is made from transgenic mice having transgenes encoding for polypeptides which can be assayed, e.g., colorimetric or histological assays, or any assay in the art able to detect and quantify beta-galactosidase and other detectable markers.

The invention also provides a cellular composition comprising an enriched population of isl1 positive stem cells. The composition preferably contains a majority of or at least about 90% isl1 positive stem cells as compared with other cell types. The isl1 positive stem cells are derived from any cardiac tissue, such as from a rat, mouse or human.

Any suitable immunoassay format known in the art and as described herein can be used to detect the presence of and/or quantify the amount of Islet 1-expressing cells in a diverse population of cells. Any type of anti-Islet 1 polypeptide antibody, which binds specifically to Islet 1 polypeptide, can be used in the invention methods, although monoclonal antibodies are preferred.

The invention immunological tests for Islet 1 polypeptide can be used in a high throughput format using any technique known in the art, such as FACS screening as is described below in greater detail.

As such, a plurality (i.e., 2 or more) different test agents, alone or in combination, may be examined for their ability to affect and/or regulate cardiogenesis. Accordingly, in various embodiments, the high throughput method is practiced by contacting multiple candidate agents with different samples of cells of different subjects; or different amounts of the same test agent with different samples of cells of different subjects; or contacting different amounts of different candidate agents with different samples of cells of two or more different subjects. Further, a high throughput format allows, for example, control samples (positive controls and or negative controls) to be run in parallel with test samples, including, for example, samples of agents known to regulate cardiogenesis. Variations of the exemplified methods also are contemplated.

When performed in a high throughput (or ultra-high throughput) format, the methods can be performed on a solid support (e.g., a microtiter plate, a silicon wafer, or a glass slide), wherein samples to be contacted with one or more test agents are positioned such that each is delineated from each other (e.g., in wells). Any number of samples or test agents (e.g., 96, 1024, 10,000, 100,000, or more) can be examined in parallel using such a method, depending on the particular support used. Where test agents are positioned in an array (i.e., a defined pattern), each agent in the array can be defined by its position (e.g., using an x-y axis), thus providing an "address" for each agent. An advantage of using an addressable array format is that the method can be automated, in whole or in part, such that candidate agents, reagents, cell samples, and the like, can be dispensed to (or removed from) specified positions at desired times, and samples (or aliquots) can be monitored, for example, for expression of isl1.

Detectable labels suitable for binding to antibodies used in the invention methods, including high throughput screening formats, include radiolabels linked to the antibodies using various chemical linking groups or bifunctional peptide linkers. A terminal hydroxyl can be esterified with inorganic acids, e.g., $^{32}P$ phosphate, or $^{14}C$ organic acids, or else esterified to provide linking groups to the label. Enzymes of interest as detectable labels will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2,3-dihydrophthalazinediones (e.g., luminol), and the like.

Antibodies may also be attached to solid supports, which are particularly useful for immunoassays or immunoprecipitation of Islet 1 polypeptide. Such solid supports include, but are not limited to, glass, cellulose, polyacrylamide, nylon, polystyrene, polyvinyl chloride or polypropylene, for example protein G covered wells of microtiter plates or beads.

Antibodies directed against a specific epitope, or combination of epitopes, so as to bind specifically with the Islet 1 polypeptide will allow for the screening of cell populations as described herein. Various screening techniques can be utilized using such monoclonal antibodies, and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737-49 (1999)).

The antibodies useful in the invention methods may be assayed for immunospecific binding by any method known in the art. The immunoassays which can be used, include but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., Western blot analysis. Those of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. Those of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. Those of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with the antibody of interest conjugated to a labeled compound (e.g., $^{3}H$ or $^{125}I$) in the presence of increasing amounts of an unlabeled second antibody.

Antibodies used in invention assay(s) can be polyclonal, monoclonal, or a functionally active fragment thereof. Mono- or poly-clonal antibodies to a islet 1 polypeptide are raised in appropriate host animals by immunization with immunogenic conjugate(s) using conventional techniques as are known in the art.

The preparation of monoclonal antibodies is disclosed, for example, by Kohler and Milstein, *Nature* 256:495-7, 1975; and Harlow et al., in: *Antibodies: a Laboratory Manual*, page 726 (Cold Spring Harbor Pub., 1988), which are hereby incorporated by reference. Briefly, monoclonal antibodies can be obtained by injecting mice, or other small mammals, such as rabbits, with a composition comprising an invention immunogenic conjugate whose preparation is disclosed above, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Barnes et al., Purification of Immunoglobulin G (IgG), in: *Methods in Mot Biol.*, 10: 79-104, 1992). Antibodies of the present invention may also be derived from subhuman primate antibodies. General techniques for raising antibodies in baboons can be found, for example, in Goldenberg et al., International Patent Publication WO 91/11465 (1991) and Losman et al., *Int. J. Cancer*, 46:310-314, 1990.

It is also possible to use anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The term "antibody" as used in this invention includes intact molecules as well as functional fragments thereof, such as Fab, F(ab')$_2$, and Fv that are capable of binding islet 1 polypeptide These functional antibody fragments are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York, 1988, incorporated herein by reference). As used in this invention, the term "epitope" means any antigenic determinant on an antigen to which the paratope of an antibody binds. Epitopic determinants usually consist of chemically active surface groupings of molecules such as amino acids or carbohydrate side chains and usually have specific three dimensional structural characteristics, as well as specific charge characteristics.

Antibody fragments according to the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., *Biochem. J.*, 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., *Proc. Nat'l Acad. Sci. USA* 69:2659-62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, *Methods*, 2: 97-105, 1991; Bird et al., *Science* 242:423-426, 1988; Pack et al., *Bio/Technology* 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, *Methods*, 2: 106-10, 1991.

The invention methods use monoclonal antibodies characterized as specifically binding to islet 1 polypeptide, wherein Islet 1 polypeptide retains functional activity.

Hybridoma cell lines producing monoclonal antibodies useful in the invention methods for immunocapture of Islet 1 polypeptide are commercially available.

The present invention is more particularly described in the following examples which are intended as illustrative only since numerous modifications and variations therein will be apparent to those skilled in the art. The following examples are intended to illustrate but not limit the invention.

EXAMPLE 1

Lineage Diversification of Isl1+ Cardiac Progenitor Cells

Isl1 plays a pivotal role in development of cardiac progenitors of the second heart field, marks postnatal progenitors in postnatal heart, and marks cardiovascular progenitor cells in the early embryo which are pluripotent in vitro. Therefore, understanding factors which regulate Isl1 expression is critical to understanding factors which drive cardiac progenitor proliferation, survival and migration, both in the context of normal development, and for potential application to cell therapies utilizing cardiac progenitors.

The purification, renewal and differentiation of native cardiac progenitors would form a mechanistic underpinning for unraveling steps for both cardiac lineage formation and regeneration, and their links to forms of congenital and adult cardiac diseases. Until now there has been little evidence for native cardiac precursor cells in the post-natal heart.

Recently, taking advantage of a developmental lineage marker for undifferentiated cardiogenic precursor cells as a requirement for a heart-specific origin, the identification of isl1$^+$ cardiac progenitors in embryonic and post-natal heart muscle of mouse, rat and human was reported (Laugwitz K-L, Moretti A, Lam J, Gruber P, Yinhong C, Woodard S, Lin L-Z, Cai C-L, Lu M, Reth M, Platoshyn O, Yuan J, Evans S & Chien K R (2005) Postnatal isl1$^+$ cardioblasts enter fully differentiated cardiomyocyte lineages. Nature 433: 647-653). During development, the transcription factor isl1 marks a cell population which makes a substantial contribution to the embryonic heart, comprising a majority of cells in the right ventricle, both atria, the outflow tract, and also specific regions of the left ventricle (Cai et al., (2003) Isl1$^+$ identifies a cardiac progenitor population that proliferates prior to differentiation and contributes a majority of cells to the heart. Dev. Cell 5: 877-889).

Isl1 expression is down-regulated as soon as the cells adopt a differentiated phenotype, suggesting the possibility that this LIM-homeodomain transcription factor delineates a cardiogenic progenitor cell population. A cardiac mesenchymal feeder layer drives progenitor cell self-renewal, maintaining their triggered differentiation into a fully mature cardiomyocytic phenotype in the absence of cell fusion. Tamoxifen-inducible Cre/lox technology allows selective in vivo marking of this progenitor cell population including its progeny, at a defined time, and purification to relative homogeneity by fluorescence-activated cell sorting (FACS). Co-culture studies with neonatal myocytes indicate that isl1$^+$ cells represent authentic, endogenous cardiac progenitors (cardioblasts) that display highly efficient conversion to a mature cardiac phenotype with stable expression of myocytic markers (25%) in the absence of cell fusion, intact Ca2$^+$-cycling, and the generation of action potentials (Laugwitz et al., 2005).

Using conditional genetic marking techniques in the mouse, Cre-recombinase-triggered cell lineage tracing experiments were performed to irreversibly mark isl1-expressing cells as well as their differentiated progeny during embryonic development. Isl1-IRES-Cre mice were crossed into the conditional Cre reporter strain R26R, in which Cre-mediated removal of a stop sequence results in the ubiquitous expression of the lacZ gene under the control of the endogenous *Rosa*26 promoter (Srinivas S. et al. (2001) Cre reporter strains produced by targeted insertion of EYFP and ECFP into the ROSA26 locus. BMC Dev. Biol. 1, 4; Soriano P (1999) Generalized lacZ expression with the ROSA26 Cre reporter strain. Nature Genet. 21, 70-71). In mice bearing both alleles beside the right ventricular and atrial myocardium, a high proportion of endothelial cells, smooth muscle cells and pericytes of the great and small epicardial coronary vessels expressed β-galactosidase (β-gal) detected by X-gal staining (FIG. 1). Basically the whole wall of the left and right coronary artery stained positive for X-gal. Additionally the same expression pattern of n-gal was observed in the wall of the aorta and the pulmonary artery in the outflow tract of double heterozygous mice.

Figures 2A, 2B:
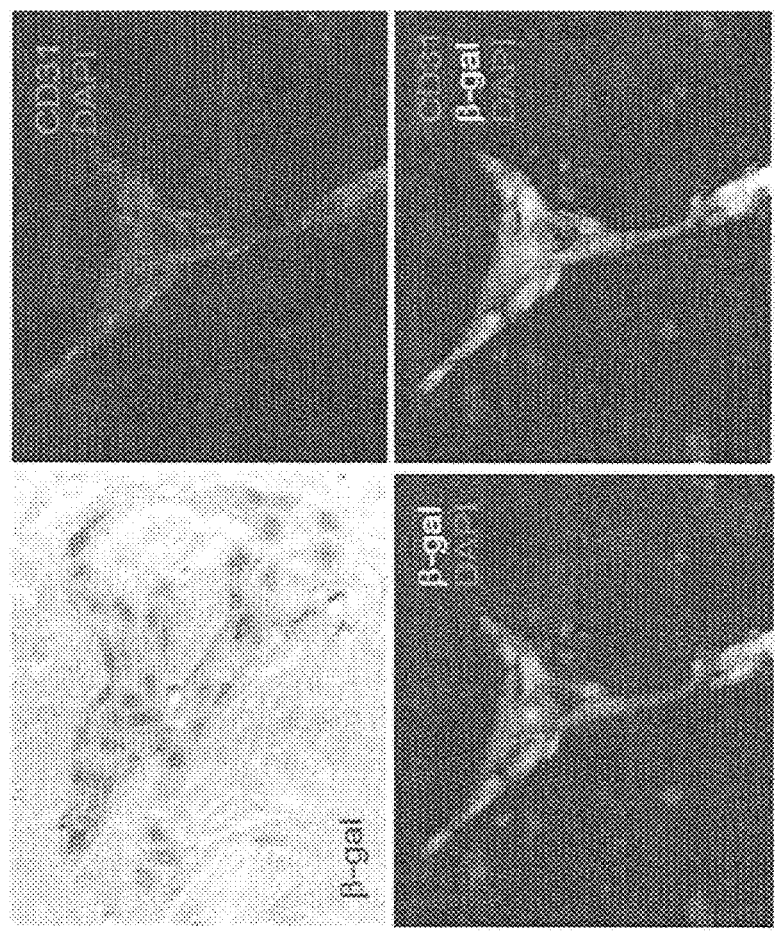
FIGS. 2A and 2B are graphical and pictorial diagrams showing a cell lineage tracing for the endothelial cell lineage of isl1+ progenitors. Mice carry one isl1-IRES-Cre allele and one R26R reporter gene. Cre expression catalyses excision of the stop cassette, resulting in selective lacZ expression and genetic marking of isl1-expressing cells and their differentiated progeny. Immunohistochemistry for β-gal (green) and CD31 (red) in isolated aortic endothelial cells from double heterozygous hearts.

To identify the specific cell types which are formed by isl1+ cardiac progenitors during aortic development in the embryo, endothelial cell fractions and smooth muscle cell fractions were isolated from the aorta of isl1-IRES-Cre/R26R mice. Around 60-70% of the endothelial cells isolated from double heterozygous aortas stained positive for X-gal and displayed coexpression of β-gal and CD31, VE-cadherin, CD 146 and von Willebrandt factor (FIGS. 2A and 2B). Additionally around 40% of the smooth muscle cell fraction showed coexpression of the genetic marker β-gal and the differentiated smooth muscle markers, smooth muscle myosin heavy chain and smooth muscle actin.

Table 1 presents an anatomical summary of the in vivo cell lineage tracing analysis for isl1+ cardiac progenitor cells. β-gal expression was observed in the conduction system, especially the Sinus node region, the endothelial and smooth muscle cells of the great vessels of the outflow tract, the left and right coronary artery and the small, epicardial coronary arteries, the intra-cardiac ganglia of the autonomic nervous system and atrial, ventricular and septal myocytes of the working myocardium (Table 1).

TABLE 1

Anatomical summary of the in vivo lineage tracing analysis

|  | β-gal expression | Lineage specific markers |
| --- | --- | --- |
| Conduction system | | |
| SA-nodal cells | +++ | acetylcholinesterase |
| AV-nodal cells | + | acetylcholinesterase |
| Purkinje cells | + | acetylcholinesterase |
| Great vessels (Ao/Pa) | | |
| Endothelial cells | +++ | CD31, VE-cadherin, CD146, vWF |
| Smooth muscle cells | +++ | smooth muscle actin, smooth muscle myosin heavy chain |
| Great conronary arteries (LCA/RCA) | | |
| Small coronary arteries (epicardial) | | |
| Endothelial cells | ++ | CD31, VE-cadherin, CD146, vWF |
| Smooth muscle cells | ++ | smooth muscle actin, smooth muscle myosin heavy chain |
| Intercardiac ganglia | +++ | acetylcholinesterase |
| Working myocardium | | |
| Atrial myocytes | +++ | α-actinin, troponin T, ANF |
| Ventricular myocytes | +++ | α-actinin, troponin T, α-myosin heavy chain |
| Septal myocytes | ++ | α-actinin, troponin T |

To address the temporal and spatial requirements for canonical Wnt signaling through β-catenin in Isl1-expressing cardiac progenitors, a Cre recombinase expressed under the control of the endogenous Isl1 locus was utilized. The early expression of Isl1-Cre in cardiogenic progenitors, and in early pharyngeal endoderm, a cardiac inducing tissue, provided the opportunity to examine the requirement for β-catenin in these tissues during early cardiogenesis.

To achieve temporal and spatial control of Cre expression required for tracing the fate of isl1+ progenitors resident in the post-natal heart, mice that harbor a knock-in of the tamoxifen-dependent Cre recombinase (isl1-mER-Cre-mER) into the genomic isl1 locus were generated. This tamoxifen-inducible Cre/lox technique enabled the selective marking of this progenitor cell population, and the subsequent purification of the β-Gal+ cells using fluorescence-activated cell sorting (FACS) after labeling the cells with a fluorogenic (3-Gal substrate (C12FDG). β-Gal+ cells can be purified from the mesenchymal cells using FACS sorting after labeling with C12FDG. Isl1+ progenitors were isolated as a distinct population presenting 7-10 times higher C12FDG fluorescence than background at a purity of 90-95%. They corresponded to 0.5% of the mesenchymal cell fraction when FACS-sorted during an early stage in culture (4-6 days) and reached ~8% after 15-18 days culture. As phenotypic characteristics of an undifferentiated state, β-Gal+progenitors expressed isl1 and early specification markers for cardiac mesoderm, Nkx2.5 and GATA-4, while lacking transcripts of mature myocytes, e.g., α-myosin heavy chain (αMHC, troponin I/T, α-actinin, myosin light chain ½ and differentiated smooth muscle markers, e.g., smooth muscle myson heavy chain and smooth muscle actin.

Figure 3:
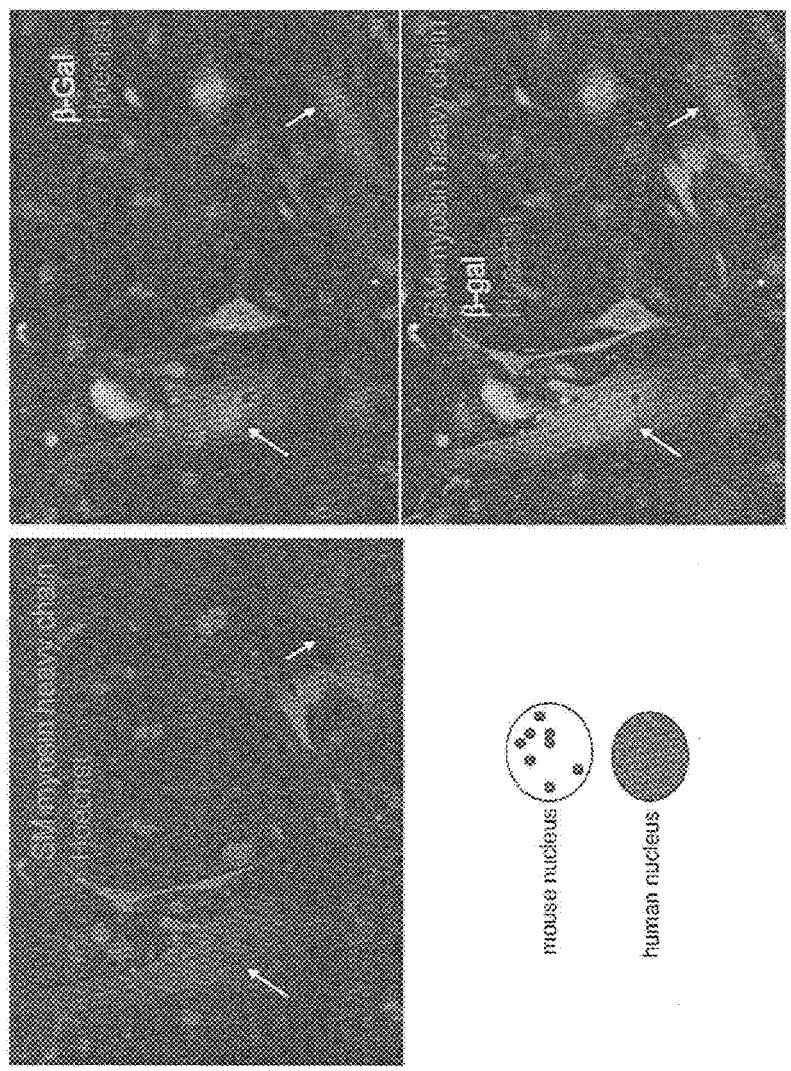
FIG. 3 is a pictorial diagram showing a cell fusion independent smooth muscle differentiation of isl1$^+$ cardioblasts in vitro. Images of differentiated β-gal$^+$ FACS purified progenitors in co-culture with human arterial smooth muscle cells. Hoechst dye labels mouse nuclei in a punctuated pattern while human nuclei are homogenously stained. The smooth muscle myosin heavy antibody is mouse specific. White arrows designate β-gal$^+$ cells of mouse origin expressing the differentiated smooth muscle marker, smooth muscle myosin heavy, shown by the red fluorescence.

Co-culture experiments of FACS-sorted precursors with human arterial smooth muscle cells (FIG. 3) were performed to assess the potential of β-Gal+ progenitors to adopt a smooth muscle phenotype. After 3-5 days in co-culture, β-Gal+ cells were found within the smooth muscle syncytium and expressed specific proteins of smooth muscle cells, i.e., smooth muscle myosin heavy chain and smooth muscle actin. In this different species system (mouse versus human) the role of cell fusion in the progenitor-to-smooth muscle transition can be easily ruled out by two experimental approaches. First the immunohistochemical analysis was performed with a mouse specific antibody for smooth muscle myosin heavy chain, and secondly, Hoechst dye easily allowed distinguishing between mouse and human nuclei by its staining pattern. These coculture experiments indicated that isl1+ cardioblasts enter the smooth muscle program independently from cell fusion (FIG. 3).

These studies documented that the LIM-homeodomain transcription factor islet-1 (isl1) represents an embryonic marker for genetically distinct populations of undifferentiated heart progenitors that give rise to all of the major muscle and non-muscle cell lineages, e.g., SA nodal, coronary arterial endothelial/smooth muscle cells, endocardium and a subset of valvular cells during embryonic development.

This genetic system should allow the rapid and direct identification of signaling pathways which guide the formation, renewal, and diversification of isl1+ progenitors into distinct heart cell lineages.

EXAMPLE 2

Wnt Signaling Function in Self-Renewal of Cardiac Progenitor Cells

The canonical Wnt cascade has emerged as a critical regulator of stem cells. Stem cells are cells that have the unique ability to self-renew as well as to generate more differentiated progeny. The most primitive stem cell is the embryonic stem cell, which is derived from the inner cell mass of the blastocyst. This cell is pluripotent and can thus generate all tissues of the body. Adult stem cells are normally involved in homeostatic self-renewal processes but can also be rapidly recruited to repair tissues upon injury, their self renewal capacity is limited. The importance of the Wnt cascade was established over the last years for stem cell maintenance and growth in the intestinal, epidermal and hematopoietic system (Reya T. & Clevers H (2005) Wnt signaling in stem cells and cancer. Nature 434, 843-850).

Wnt genes, of which the human genome harbours almost 20, occur throughout the animal kingdom (Veernan M T, Axelrod J D & Moon R T A (2003) A second canon. Functions and mechanisms of b-catenin-dependent Wnt signalling. Dev. Cell 5: 367-377). Signaling is initiated when Wnt ligands engage their cognate receptor complex, consisting of a heptahelical receptor of the Frizzled family and a member of the LDL receptor family, Lrp5/6. The central player is a cytoplasmic protein termed β-catenin, the stability of which is regulated by the destruction complex containing the tumor suppressor adenomatous polyposis coli (APC) and axin. CKI and GSK3β, two kinases residing in the destruction complex, then sequentially phosphorylate a set of conserved Ser and Thr residues in the amino terminus of β-catenin. The resulting phosphorylated footprint recruits a β-TrCP-containing E3 ubiquitin ligase, which targets β-catenin for proteasomal degradation.

Receptor occupancy inhibits the kinase activity of the destruction complex by an incompletely understood mechanism involving the direct interaction of axin with Lrp5/6, and/or the actions of an axin-binding molecule, dishevelled. As a consequence, β-catenin accumulates and travels into the nucleus where it engages the N terminus of the DNA-binding proteins of the Tcf/Lef family. This process initiates the transcription of Wnt dependent target genes (Eastman, Q. & Grosschedl, R (1999) Regulation of LEF-1/TCF transcription factors by Wnt and other signals. Curr. Opin. Cell Biol. 11, 233-240).

Figures 4A, 4B:
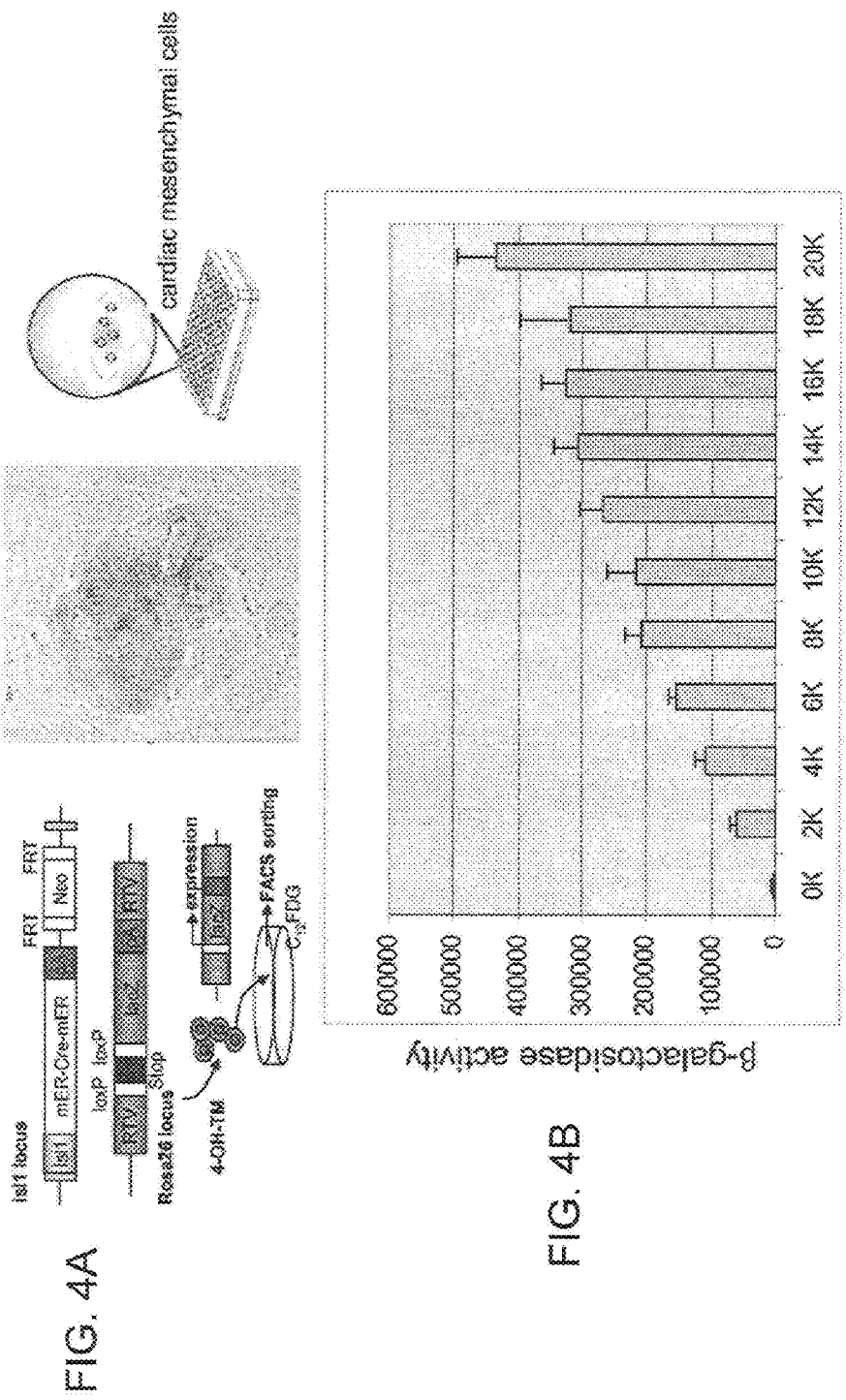
FIGS. 4A and 4B are pictorial and graphical diagrams showing a chemical compound screen with β-gal$^+$ cardiac progenitors from the isl1-mER-Cre-mER/R26R genetically tagged mice. Tamoxifen injection of isl1-mER-Cre-mER/R26R double heterozygous mice or administration of 4-OH-TM in culture results in heritable expression of lacZ the precursor cell population. Mesenchymal cell fractions from the genetic labeling system exhibit β-gal$^+$ cardioblasts after X-gal stain. Different cell densities of the mesenchyme fraction results in a linear correlation with β-galactosidase activity detected by the luciferase assay.

The inventors developed an assay based on the β-gal tagged cardiac progenitors to identify small molecules and defined factors that can trigger the renewal of the cardiac progenitors (FIGS. 4A and 4B). The isl1-mER-Cre-mER knock-in mice were utilized to conditionally mark embryonic and post-natal isl1+ cardiac progenitors. Mice which are double heterozygous for the isl1-mER-Cre-mER and the R26R-indicator allele allow the purification of a relatively homogeneous population of isl1+ cardiac progenitors after amplification on mesenchymal feeder layers.

The β-gal substrate 6-O-β-galactopyranosyl-luciferin allows luciferase-mediated detection of light emission in genetically lacZ labelled cells in a high throughput manner (FIGS. 4A and 4B). 6-O-galactopyranosyl-luciferin is cleaved by (3-gal into D-Luciferin, which is processed by luciferase in an ATP-dependent step into Oxyluciferin and light.

Isolated cells from double heterozygous mice demonstrated a linear relationship between cell number and luciferase activity (FIGS. 4A and 4B). After screening a small molecule library containing over 15,000 compounds, a series of compounds that can trigger the expression of lacZ activity as well as the induction of the isl1 protein in cultured cardiac progenitor preparations was identified.

The screen was based on three independent read-out systems. First, the chemical compound library was screened for luciferase activity, and thereby indirectly for β-gal activity of proliferating cells. Second, β-gar progenitor cells were counted within the mesenchymal feeder layers with and without compound treatment, and third, expression of the transcription factor isl1[+] per progenitor cell was screened in an immunohistochemically based analysis.

Interestingly, these studies pointed to a critical role of Wnt signaling in the renewal pathway, since the GSK-3b inhibitor BIO had a significant effect by 50-80 fold on the proliferation capacity of isl1[+] cardiac progenitor cells. Direct studies with purified Wnt ligands have now confirmed a selective subset of these factors as mediating the renewal/proliferation of the progenitors.

Figure 6:
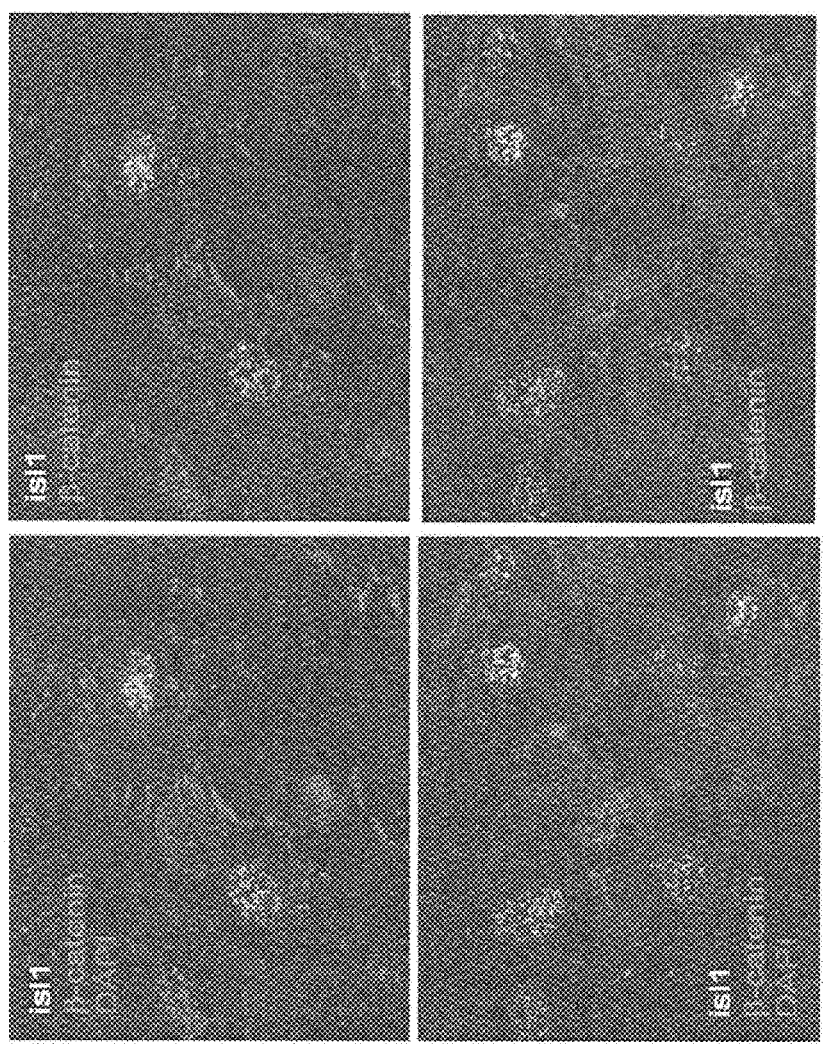
FIG. 6 is a pictorial diagram showing images of cardiac isl1+ cells on the mesenchymal feeder layer. The isl1+ cells showed activated β-catenin signaling as demonstrated in the cytosolic and nuclear localization of the protein. Yellow fluorescence designates isl1 expression in the nucleus of the progenitor cells while the red fluorescence detects β-catenin. DAPI stain is shown in blue.

In isl1-eGFP BAC transgenic mice the progenitors in the anterior heart field displayed coexpression of e-GFP and β-catenin. Additionally, a higher expression of β-catenin was observed in the cytosol and nuclei of proliferating isl1+ progenitor cells within the cardiac mesenchyme after cell isolation from embryonic and postnatal hearts, indicating active β-catenin signaling within the cardiac precursor pool (FIG. 6).

The results provided herein demonstrate that β-catenin directly targets and activates Isl1 expression. It was observed that a correspondence exists between active β-catenin signaling and regions of Isl1 expression in progenitors of the second heart field including regions harboring Isl1/flk1/Nkx2.5 progenitors, in pharyngeal endoderm, and in regions within the heart where persistent Isl1 expression has been observed. Isl1 expressing cells isolated from postnatal hearts are capable of expansion in culture, and can differentiate to functional cardiomyocytes. Isl1/flk1/Nkx2.5-expressing cells clonally isolated from embryonic stem cells or embryos can be amplified and give rise to endothelial, smooth muscle, or cardiac lineages. Factors which are required upstream of Isl1 for proliferation, however, have not been defined. Thus, the results demonstrate a critical role for β-catenin in proliferation of Isl1-expressing progenitors.

The results further demonstrate a key role for β-catenin in outflow tract morphogenesis, in formation of the atrial septum, and in atrio-ventricular cushion formation. With regard to the latter, the findings herein are consistent with expression of Isl1 in endocardial cells which contribute to cushion formation, and previous data which demonstrated that ablation of O-catenin in endothelial cells disrupts epithelial-mesenchymal transformation and cushion formation. Requirements for β-catenin in cushion formation and septation have also been demonstrated in chick and zebrafish. The observed requirement for β-catenin in atrial septation is consistent with downregulation of Isi1, Shh and Pitx2, as mutants affecting expression of these genes also have defects in atrial septation. The atrial septal defects in the Isl1-Cre, β-catenin mutant, however, appear to be quite distinctive, with two truncated septal primordia observed in the dorsal aspect of the atrial wall.

Decreased proliferation within secondary/anterior heart field has been demonstrated to result in outflow tract defects. As Isl1 expression is downregulated in β-catenin mutants, and as Isl1 is required for proliferation within the secondary/anterior heart field, it is likely that decreased Isl1 expression in the secondary/anterior heart field and its derivatives, as observed here, are contributing to observed outflow tract defects. Indeed, it was observed that similar cardiac phenotypes to those of the Isi1-Cre, β-catenin mutants in hypomorphic mutants of Isl1.

Cardiac neural crest cells are also required for outflow tract morphogenesis, and can affect proliferation of the secondary heart field. Expression of Isl1 in wnt1-Cre; R26R-lacZ lineage traced cardiac neural crest cells was not observed within the outflow tract, although Isl1 is expressed within intrinsic cardiac ganglia which derive from the cardiac neural crest. From this, and a comparison of results with Wnt1-Cre and Isl1-Cre (unpublished studies), it is unlikely that Isl1 lineages contribute to the cardiac neural crest population that will contribute smooth muscle cells to the outflow tract, aorta or pulmonary artery.

Thus, the outflow tract phenotype of Isl1-Cre; β-catenin mutants is unlikely to be owing to ablation of β-catenin within cardiac neural crest that will directly contribute cells to the aorta and pulmonary artery. However, it is possible that ablation of β-catenin within Isl1 expressing domains secondarily affects this population of cardiac neural crest cells and in this manner contributes to observed outflow tract phenotypes. Consistent with the latter possibility, decreased levels of PlexinA2 expressing cells were observed within the outflow tract of Isl1-Cre, β-catenin mutants relative to littermate controls.

In addition to decreased expression of Isl1 in Isl1-Cre; β-catenin mutants, downregulation of a number of other genes required for outflow tract morphogenesis was observed, including Shh, Wnt11, Pitx2, Tbx2 and Tbx3. Selective decreases were observed in Tbx3 expression within the mandibular arch, and aortic arch regions, and in Tbx2 expression in the outflow tract of Isl1-Cre, β-catenin mutants. Both Tbx2 and Tbx3 are required for outflow tract formation.

Active β-catenin signaling was observed within both the pharyngeal endoderm and the cardiac mesoderm, suggesting a potential role in both. Previous ablation of β-catenin with a Cytokeratin-19 promoter driven Cre resulted in ectopic heart formation, which was attributed to ablation β-catenin in pharyngeal endoderm. Despite ablation of β-catenin signaling in early ventral pharyngeal endoderm by Isl1-Cre, ectopic heart formation was not observed. The Cytokeratin-19 promoter may be expressed earlier than Isl1 in ventral endoderm, or an expression domain of the Cytokeratin-19 promoter which is distinct from that of Isl1 is responsible for the observed phenotype.

It was found that β-catenin was required within the Isl1 domain for branchial arch formation and aortic arch artery formation. In Isl1-Cre; β-catenin mutants, the mandibular arch was severely hypomorphic, as were left aortic arch arteries, and the 4th PAA was absent. A similar phenotype is observed in Isl1 hypomorphs, and in mutants of the Shh pathway. It was previously demonstrated that expression of Shh in pharyngeal endoderm is downstream of Isl1. Similar apoptotic profiles are observed in Shh mutants, in Isl1-Cre; smoothened mutants, and are described here in Isl1-Cre; β-catenin mutants. Together, these data suggest a genetic cascade with β-catenin upstream of Isl1, and Isl1 upstream of Shh for pharyngeal arch development. β-catenin may also regulate Shh independently of Isl1.

It was also previously shown that Shh is downstream of Isl1 in a signaling pathway required for outflow tract morphogenesis. Results of this study demonstrate that β-catenin is a key upstream factor which drives expression of isl1 in cardiac progenitors and their proliferation and survival, and is also upstream in genetic cascades which regulate diverse aspects of pharyngeal arch and cardiac morphogenesis (see FIG. 15). Wnt ligands, which regulate this pathway are currently unknown. Wnt2 is expressed in the cardiogenic crescent, and may act redundantly with other Wnts upstream of β-catenin in this context.

It will now become possible to directly decipher the signaling pathways for self-renewal within the isl1+ cardiac progenitor system.

EXAMPLE 3

β-Catenin Regulates Islet1 Expression in Cardiovascular Progenitors

Floxed β-catenin mice were obtained from the Max-Planck-Institute of Immunobiology. Isl1-Cre mice were created by a Cre knock-in into the endogenous Isl1 locus, replacing the endogenous Isl1 ATG. Homozygous Boxed β-catenin mice were crossed with Protamine-Cre mice to generate β-catenin+/−mice, which were then crossed with Isl1-Cre mice to produce doubly heterozygous Isl1-Cre+/−; β-catenin+/−mice. These mice were then crossed to β-catenin floxed/floxed homozygous mice to obtain Isl1-Cre+/−; β-cat-/f mutants for analysis.

Whole-mount RNA in situ hybridization and histological analyses. Whole-mount RNA in situ hybridization was carried out as previously described. References for specific RNA in situ probes are as follow: Isl1 (EST, GenBank Accession No.: AA198791), Tbx2, Tbx3 and Pitx2 were from the Institute of Neurosciences, University of Padua, Padua, Italy; Wnt11 was from The Department of Molecular and Cellular Biology of Harvard University; PlexinA2 was from the University of Pennsylvania Medical School; Fgf8 was from Gail Martin; Shh was from the University of California, San Francisco. For histological analyses, embryos were fixed in 4% paraformaldehyde, dehydrated in ethanol, embedded in paraffin, 8 μm sections prepared on a microtome, and stained with hematoxylin-eosin according to standard protocols. For ink injection, embryos were collected and injected intracardially with India ink. All experiments were repeated a minimum of three times to ensure statistically relevant findings.

RNA isolation and Real-Time qPCR analyses. Total RNA was isolated from hearts and pharyngeal arch of E9.5 embryos by RNeasy kit, Qiagen. Semi-qPCR was carried out according to the Mx3000P Real-Time PCR Systems manual and the Brilliant qPCR reagent (Stratagene). The mRNA levels of Pitx2, Wnt11, Shh, Isl1, Tbx3 and Tbx2 were normalized to the mRNA levels of HPRT to allow comparisons among different experimental groups.

X-Galactosidase staining of mouse embryos. Mouse embryos were fixed in 4% paraformaldehyde for 30 min on ice, permeabilized in PBS containing 0.02% Nadeoxycholate and 0.01% NP-40 for 4 h at room temperature and then subjected to 5-bromo-4-chloro-3-indolyl-D-galactoside (X-gal) staining for 1-2 hours.

Chromatin immunoprecipitation (ChIP) assays. For in vivo ChIP experiments, extracts were prepared from 20 E9.0-9.5 wildtype mouse embryo hearts. Embryos were dissected in ice-cold PBS. Following gentle pipetting, tissue was cross-linked with 2% formaldehyde for 2 hours at room temperature. Chromatin extraction and immunoprecipitations were performed according to the manufacture's protocols by using a ChIP assay kit (Upstate, 17-295). Protein-DNA cross-linking was reversed by overnight incubation at 65° C. A PCR purification kit (QIAGEN, 28106) was used to recover DNA in 50 μl. The following PCR primers against the 5' Isl1 promoter region were used: primer P-2940 (5'-GCG CCA GGA ACT GTG CTC CAA-3') (SEQ ID NO 1) and primer P-2630 (5'-AGG GGC GAC CTC TTG TGT TCA ATG-3') (SEQ ID NO: 2), primer P-850 (5'-GAA CAG GAG ACC TCA CGG GTC GGG-3') (SEQ ID NO: 3) and primer P-534 (5'-CTA GCA GCG CGC TAC GCG TTA GGG-3') (SEQ ID NO: 4), primer P-15 (5'-GAA GAG AGG TGC CCC GAG CCG TGC-3') (SEQ ID NO: 5) and primer P-290 (5'-TTT GGT GGA TCG CCC ATG TCT CCC-3') (SEQ ID NO: 6), primer P790 (5'-CCC GCG TGC TAT TGA AGA ACG TGC-3') (SEQ ID NO: 7) and primer P1070 (TTG GGA TGG TAA TTG GAG TGT GCC-3') (SEQ ID NO: 8). β-catenin antibody was obtained from Santa Cruz Biotechnology.

Promoter cloning and luciferase transfection assays. A 5.0 genomic DNA fragment upstream of Isl1 start codon was amplified with a high fidelity DNA polymerase (Novagen, 71086-3) and was cloned into pGL3-basic vector (Promega, E1751). Primers were: 5' primer 5'-GATGGTACCCTCAAC-TAA ATGAGGCTAC-3' (SEQ ID NO: 9), 3' primer 5'-ATIGTCGACTTGTAAGAGGGAGTAATGTC-3' (SEQ ID NO: 10). The QuickChange sited-directed mutagenesis kit (Stratagene, 200518) was used to make point mutation in the conserved LEF-1 binding site in the Isl1 5'-promoter region according to the manufacture's protocol. Transfections were carried out in HEK 293 cells according to standard techniques by FUGENE6 (Roche). Cells were lysed 48 hr after transfection, luciferase and β-galactosidase activities were measured on a Luminoskan Ascent luminometer (Thermo Labsystems). For luciferase reporters, CMV-β-galactosidase was used to control for transfection efficiency. Normalized luciferase activities were compared with a pGL3 control to calculate the fold of activation. Data are presented as fold activity over basal promoter activity (relative activity), and are expressed as mean±SD of triplicates from a representative experiment.

Immunohistochemstry. Mouse embryos were saturated with 20% sucrose, frozen in OCT and 8 μm sections prepared on a cryotome. Sections were fixed in 2% paraformaldehyde for 10 min at room temperature, blocked with 5% serum, and stained with antibodies. Reference for antibodies are rabbit anti-phospho-histone H3 antibody (#06-570, Upstate Biochem), rabbit anti-cleaved Caspase-3 (#9661, Cell Signaling Technology), rabbit anti-β-catenin (ab6302, abeam), mouse anti-Isl1 (39.4D5, Hybridoma Bank). Secondary antibodies were goat anti-rabbit 488, donkey anti-mouse 488, donkey anti-rabbit 594 (all Alexa Fluor was used at 1:250, Molecular Probes). All experiments were repeated a minimum of three times to ensure statistically relevant findings.

Statistical Evaluations. Student's t test was used for statistical comparisons when appropriate, and differences were considered significant at $P<0.05$.

Figures 7A, 7B, 7C, 7D, 7E, 7F, 7G, 7H, 7I, 7J, 7K, 7L:
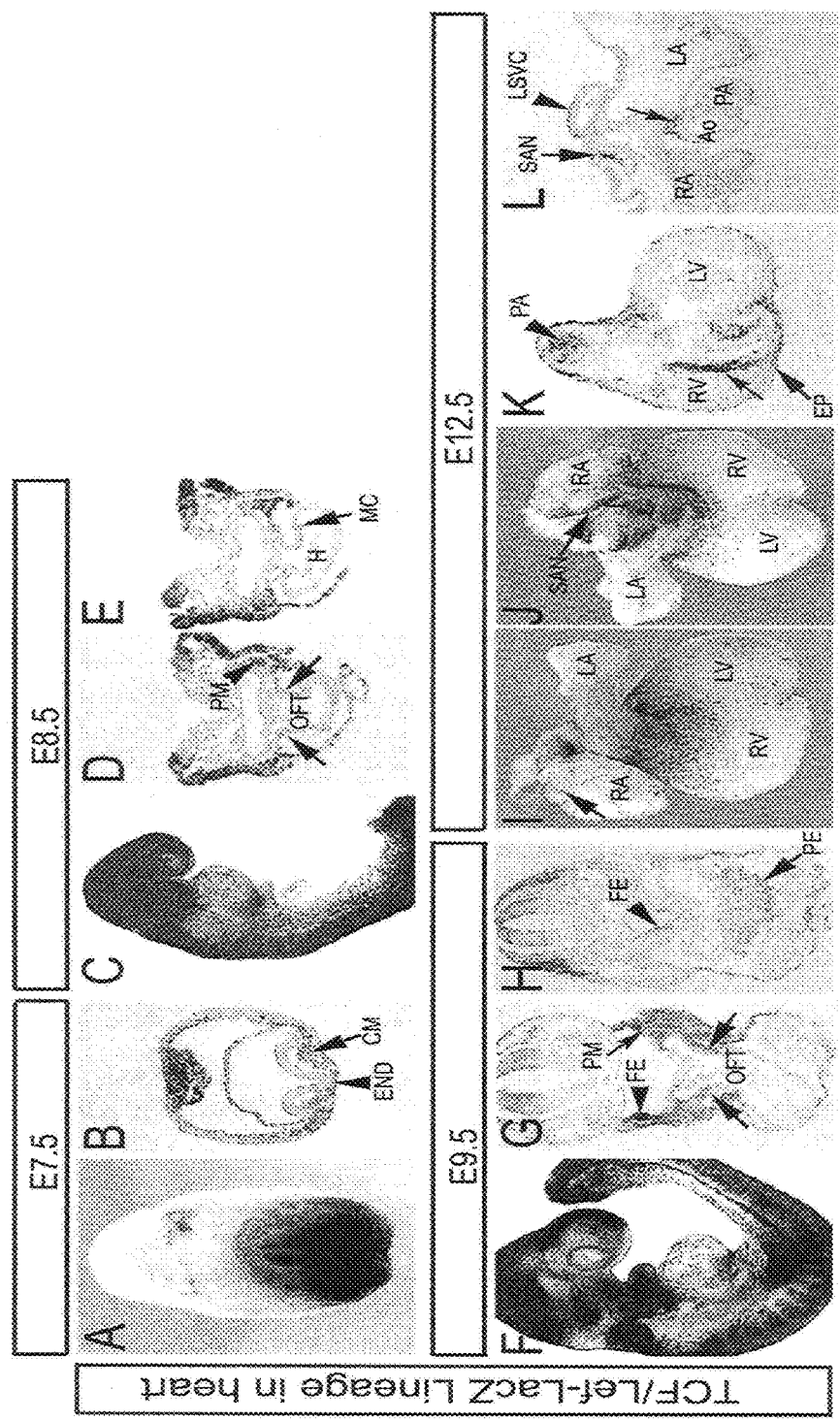
FIGS. 7A-7L are pictorial diagrams showing expression of a TCF/Lef-LacZ transgene in mouse embryos. Within FIGS. 7A-7L, the following abbreviations mean: END, endoderm; CM, cardiac mesoderm; PM, pharyngeal mesoderm; FE, Foregut endoderm; OFT, outflow tract; RA, right atrium; LA, left atrium; RV, right ventricle; LV, left ventricle; PE, pro-epicardium; EP, epicardium; PA, pulmonary artery; SAN, SA node; LSVC, left superior vena cava.

Activation of β-catenin during early cardiogenesis. To investigate where and when β-catenin signaling was occurring in the early embryo, a TCF/Lef-lacZ reporter line was utilized (FIGS. 7A-7L). Expression of TCF/Lef-LacZ (FIGS. 7A and 7B) was detected in cardiogenic mesoderm (arrow) and adjacent endoderm (arrow head) at E7.5; (FIGS. 7C-7E) at E8.5, TCF/Lef-LacZ was expressed in pharyngeal mesoderm (FIG. 7D, arrow head), outflow tract (FIG. 7D, arrows) and myocardium (FIG. 7E, arrow); (FIGS. 7F-7H) at E9.5, TCF/Lef-LacZ was expressed in foregut endoderm (FIGS. 7G and 7H, arrow heads), outflow tract (FIG. 7G, bigger arrows), pharyngeal mesoderm (FIG. 7G, smaller arrow) and pro-epicardium (FIG. 7H, arrow); (FIGS. 7I-7L) at E12.5, TCF/Lef-LacZ was strongly expressed in cells surrounding the outflow tract region, in right atria and the region of the sinoatrial (SA) node. (FIGS. 7K and 7L). Section analyses demonstrated that TCF/Lef-LacZ was expressed in right ventricle, epicardium, pulmonary artery, aorta, and in the region of the SA node.

Results of this analysis demonstrated β-catenin activation in early cardiogenic mesoderm and adjacent endoderm at E7.5 (FIGS. 7A and 7B). At E8.5 (FIGS. 7C-7E), expression of the reporter was observed in pharyngeal mesoderm, outflow tract myocardium, and at low levels in pharyngeal endoderm. At E9.5 (FIGS. 7F-7H), expression in pharyngeal mesoderm and outflow tract myocardium was striking, with expression also observed in lateral and ventral pharyngeal endoderm, and in proepicardium. At E12.5 (FIGS. 7I-7L), TCF/Lef-lacZ reporter expression was observed in epicardium, and in subsets of cells within the outflow tract and ventricles. Expression was also observed in venous valves within the right atrium, and in the region of the sinoatrial node.

To confirm results obtained with X-gal staining, immunostaining of sections was performed with antibody to β-galactosidase. Contribution of Isl1 lineages to atrioventricular cushions as indicated by immunostaining with anti-β-galactosidase antibody in Isl1-Cre; R26R-lacZ lineage traced embryos. Results demonstrated that Isl1 lineages contribute to endocardium and extensively to atrio-ventricular cushion (AVC) mesenchyme at E10.5 as observed from sections of Isl1-Cre; R26R-LacZ embryos (FIG. 7A). Higher magnification of the AVC shown in A. Anti-β-galactosidase antibody staining is shown in green and nuclei are shown in blue (DAPI) (FIG. 7B). These results are consistent with those previously observed with X-gal staining.

Ablation of β-catenin with Isl1-Cre results in early embryonic lethality and cardiac and pharyngeal arch artery defects. With the exception of the epicardium, regions where β-catenin signaling was active during cardiogenesis were overlapping with Isl1 expression, or with Isl1-derived lineages. Therefore β-catenin was ablated utilizing an Isl1-Cre. Isl1-Cre; β-catenin mutants were embryonic lethal. Examination of 12 litters with a total of 89 embryos demonstrated that 100% of Isl1-Cre; β-catenin mutants died at approximately E13.0. In contrast, control littermates of all other genotypes were completely normal and survived postnatally with no apparent phenotypic abnormalities.

Figures 8A, 8Q:
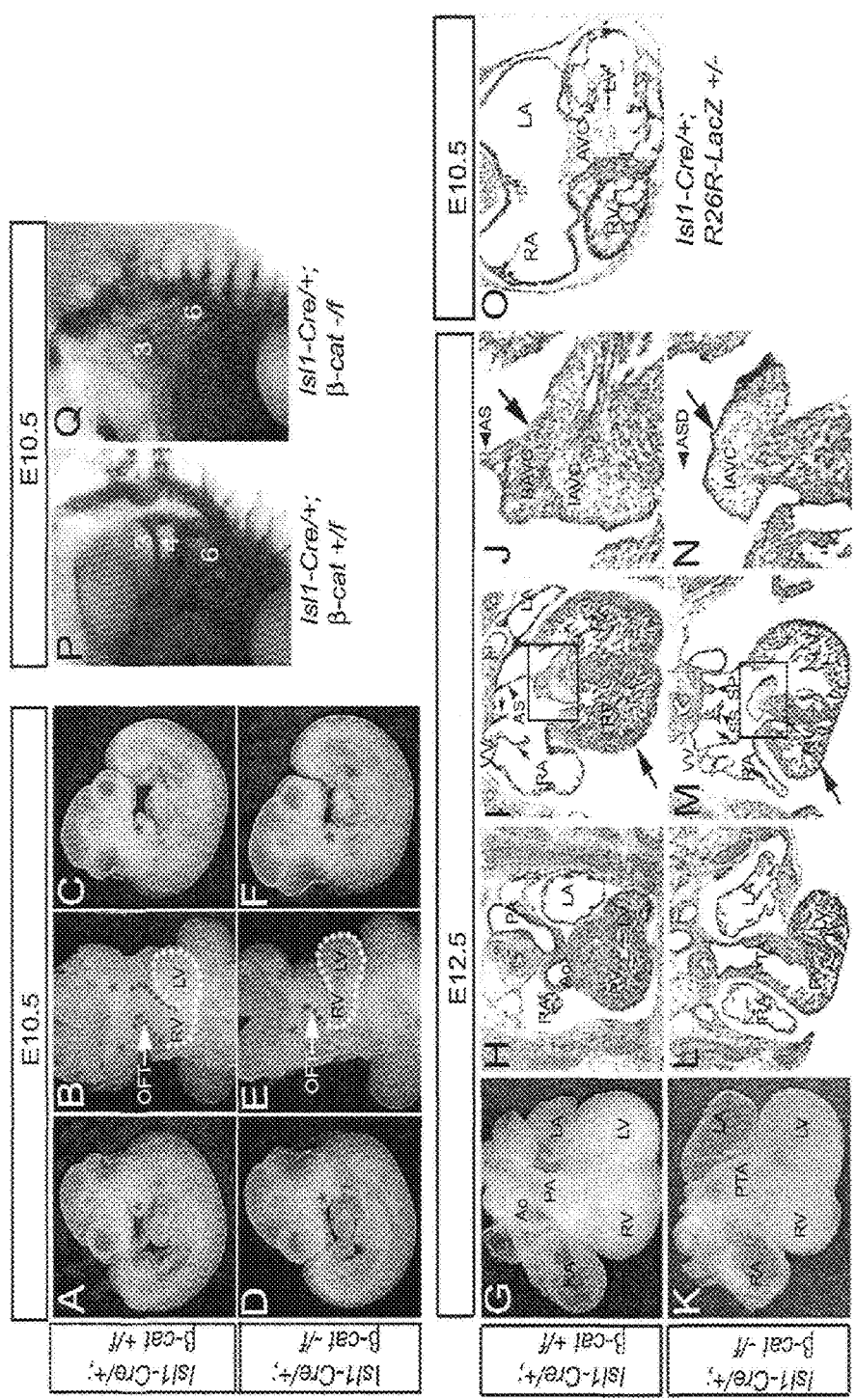
FIGS. 8A-8Q are pictorial diagrams showing ablation of β-catenin with Isl1-Cre results in embryonic lethality, abnormal cardiac morphology, and pharyngeal arch defects. Within FIGS. 8A-8Q, the following abbreviations mean: Ao, aorta; PA, pulmonary artery; AS, atria septum; ASD, atrial septal defect; VV, venous valve; AVC, atrio-ventricular cushion; SAVC, superior atrio-ventricular cushion; IAVC, inferior atrio-ventricular cushion; PTA, persistent truncus arteriosus; SP, septum primum; SS, septum secundum; PAA, pharyngeal arch artery.

Morphological analysis of mutants and control littermates demonstrated abnormal cardiac morphogenesis of mutants at E10.5, with mutant hearts exhibiting dilated outflow tracts and smaller right ventricles, and thin-walled myocardium (FIGS. 8A-8F). Isl1-Cre; β-catenin mutants exhibited 12.4% increase in diameter of the outflow tract, and right ventricles in mutants were on average 9.5% smaller as compared to control littermates. Size differences between control and mutant outflow tract and right ventricle were found to be significant with p values <0.05. Hypomorphic mandibles were also observed in mutants. (FIG. 8E). Whole-mount and section analysis shows that at E12.5, Isl1-Cre; β-catenin mutants exhibited persistent truncus arteriosus (PTA) (FIGS. 8G-8N). Section analysis demonstrated that Isl1-Cre; β-catenin mutants exhibited thinner ventricular walls, atrial septal defects, hypomorphic right ventricle, had smaller inferior atrio-ventricular cushions, and were missing superior atrio-ventricular cushions. FIGS. 8J and 8N show atrio-ventricular cushions highlighted in FIGS. 8I and 8J. Lineages studies for the Isl1 expressing progenitors by X-gal staining counterstained with Eosin (FIG. 8O) on E10.5 cardiac sections. Isl1 cells were observed within endocardium and contributed extensively to atrio-ventricular cushion mesenchyme at E10.5. (FIGS. 8P and 8Q). Ink injection shows left sided PAA defects in Isl1-Cre; β-catenin mutants, with smaller PAM 3 and 6, and no apparent 4th PAA (arrowhead) at E10.5 embryos.

Measurements performed utilizing ImageJ software on sections from three mutants and three control littermates at E 10.5 demonstrated that outflow tracts in mutants were dilated compared to control littermates. Isl1-Cre; β-catenin mutants also had smaller right ventricles. Hypomorphic mandibles, derived from the first pharyngeal arch, where Isl1 is expressed, were also observed in mutants (FIGS. 8A-8F). At E12.5, persistent truncus arteriosus (PTA), a single undivided outflow tract, was observed in mutants. Formation of atrial septal structures was aberrant, with thickened septum secundum and septum primum primordia, and no apparent septum primum (FIGS. 8G-8N). In mutants, the superior atrio-ventricular cushion was missing, and the inferior atrio-ventricular cushion was smaller, with approximately 30% fewer mesenchymal cells relative to wildtype littermates (FIGS. 8I, 8J, 8M, 8N). Affected structures arise at least in part from Isl1 expressing progenitors, as indicated by E10.5 cardiac sections from Isl1-Cre; R26R-LacZ lineage traced animals, demonstrating that more than 50% of mesenchymal cells within the atrio-ventricular cushions derive from Isl1-expressing cells (FIG. 8O). The latter observation was confirmed by immunostaining for β-galactosidase protein.

Isl1 mRNA is downregulated in Mesp1-Cre; β-catenin mutants. Whole mount mRNA in situ analysis of Mesp1-Cre; β-catenin mutants (FIG. 8B) and control littermates (FIG. 8A) at E9.0. Isl1 expression is decreased in mutants relative to control littermates. Ink injections were performed to examine pharyngeal arch artery (PAA) structure, and demonstrated left sided PAA defects in Isl1-Cre; β-catenin mutants, with smaller PAAs 3 and 6, and no apparent 4th PAA (FIGS. 8P and 8Q).

Potential downstream effector targets of β-catenin during cardiogenesis and branchial arch formation. To identify potential downstream effector targets of β-catenin, a number of genes known to be required for branchial arch, outflow tract, and atrial septal morphogenesis were examined by whole mount RNA in situ hybridization analysis, and by Real Time qPCR analysis of RNA extracted from cardiogenic regions at comparable stages to those examined by in situ. Genes examined included Isl1, Wnt11, Tbx2, Tbx3, Shh, Pitx2, and Fe. Results demonstrated that expression of Isl1, Wnt11, Pitx2, and Tbx3 was selectively downregulated in Isl1-Cre; β-catenin mutants relative to expression observed in littermate controls (FIGS. 9 and 10).

Figures 9A, 9Z:
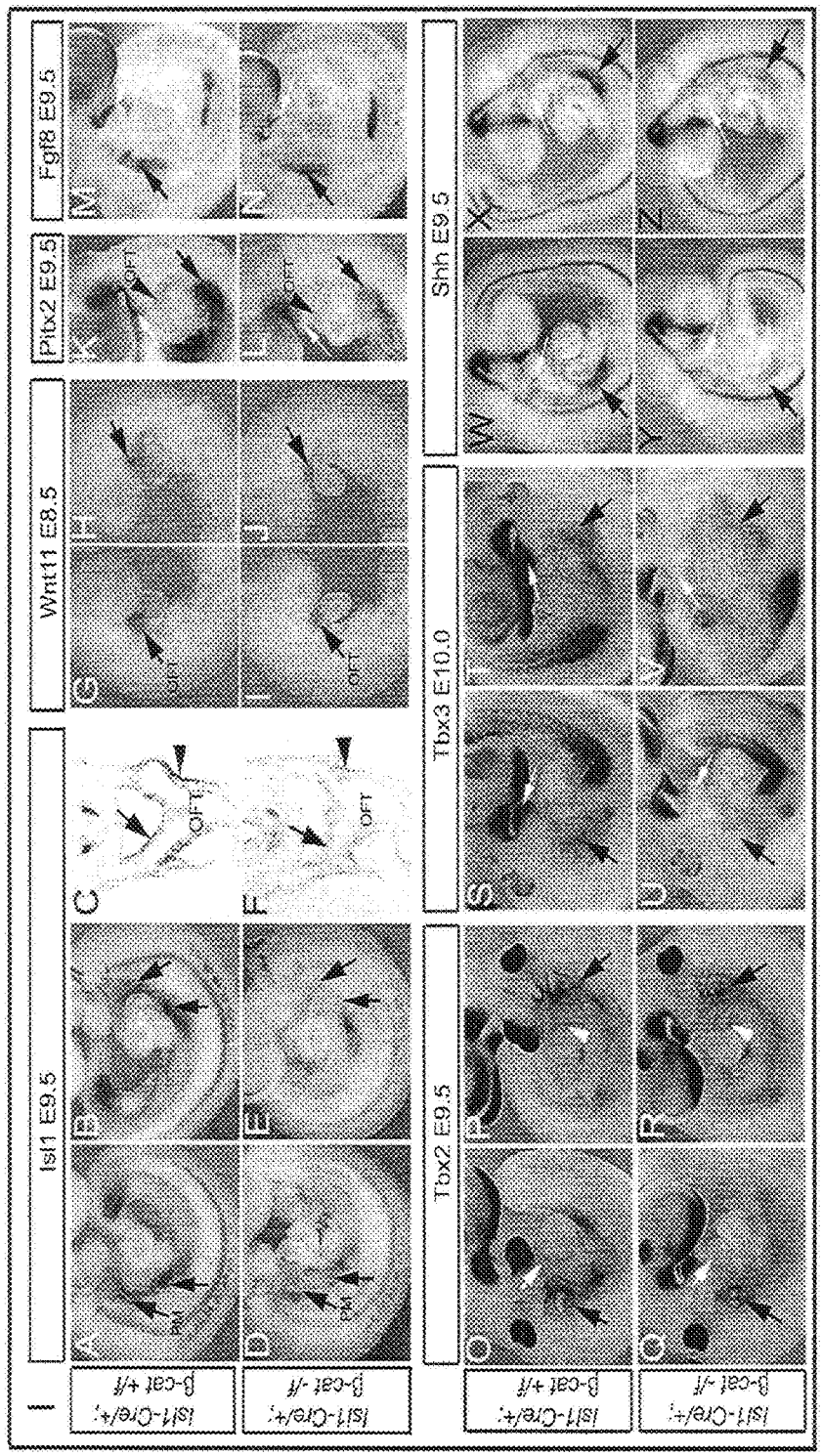
FIGS. 9A-9Z are pictorial diagrams showing analysis of potential downstream effector targets in Isl1-Cre; β-catenin mutants and control littermates. Results from whole mount RNA in situ hybridization assays.

Expression of Isl1 (FIGS. 9A-9F); Wnt11 (FIGS. 9G-9J); Pitx2 (FIGS. 9K and 9L); Fgf8 (FIGS. 9M and 9N); Tbx2 (FIGS. 9O-9R); Tbx3 (FIGS. 9S-9V) and Shh (FIGS. 9W-Z) was examined in Isl1-Cre; β-catenin mutants and littermate controls. (FIGS. 9A-9E). Isl1 was downregulated in pharyngeal region posterior to the heart (arrows). Section analysis demonstrated decreased Isl1 expression in foregut endoderm (arrows) and in splanchnic mesoderm (arrow heads) in Isl1-Cre; β-catenin mutants relative to control littermates (FIGS. 9C and 9F). In Isl1-Cre; β-catenin mutants, Wnt11 was downregulated in outflow tract (arrows) (FIGS. 9G-9J); Pitx2 was downregulated in outflow tract (arrows) and pharyngeal arches (smaller arrows) (FIGS. 9K and 9L); Expression of Fgf8 was unaffected (FIGS. 9M and 9N); Expression of Tbx2 was reduced in the outflow tract (smaller arrows) of Isl1-Cre, β-catenin mutants and but was not downregulated in AV canal (arrowheads) or pharyngeal arches (bigger arrows) (FIGS. 9O-9R); Tbx3 was downregulated in pharyngeal arches (smaller arrows) and foregut endoderm (arrows) (FIGS. 9S-9V); and Shh was downregulated in anterior foregut endoderm (arrows) and posterior foregut endoderm (smaller arrows) (FIGS. 9W-9Z). Thus, Tbx2 expression in outflow tract but not in the region of the aortic arches was decreased in mutants, whereas Fgf8 was still expressed.

Total RNA was prepared from hearts and pharyngeal arch of E9.5 embryos either control or Isl1-Cre; β-catenin mutants and analyzed by real-time RT-PCR. The mRNA level of each gene was normalized against the mRNA level of HPRT (FIGS. 10A-10F). Data obtained from three independent experiments, are shown as the means±the standard deviation.

Isl1 is a direct downstream target of β-catenin. In Isl1-Cre; β-catenin mutants, expression of Isl1 was strongly downregulated. Ablation of Isl1 in germline knockouts results in embryonic lethality at E10, and severely abnormal heart formation, with mutant hearts missing the outflow tract and right ventricle, and having severely reduced atrial tissue. It was found that a hypomorphic mutant of Isl1 exhibits embryonic lethality at E12.5, with outflow tract defects comparable to those observed with Isl1-Cre; β-catenin mutants. As these observations suggested that Isl1 is a key effector target of β-catenin for cardiac morphogenesis, it was further investigated whether Isl1 was a direct downstream target of β-catenin.

Figures 11A, 11P:
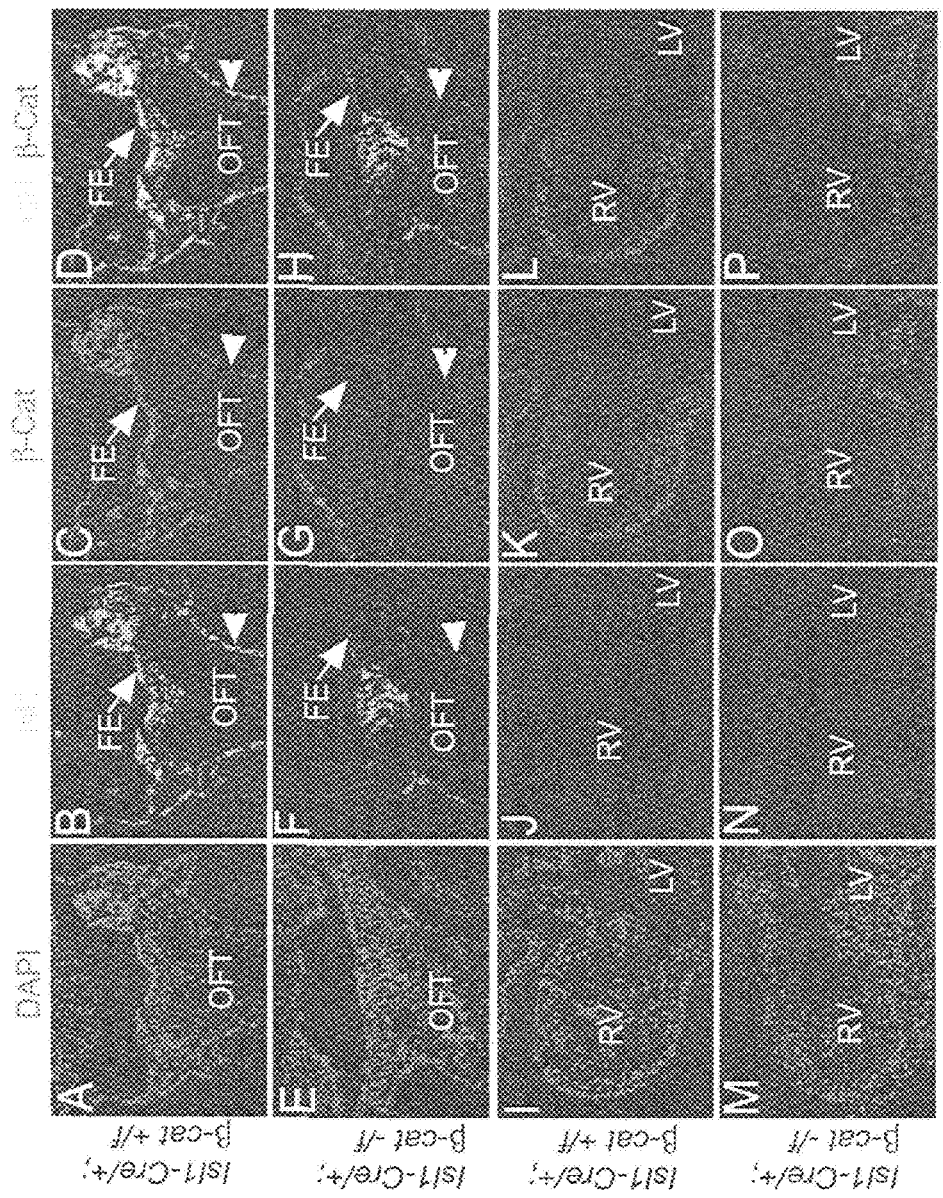
FIGS. 11A-11P are pictorial diagrams showing that β-catenin is efficiently ablated in Isl1 expressing lineages or their descendents, including foregut endoderm, OFT myocardium and RV myocardium in Isl1-Cre; β-catenin mutants. Within FIGS. 11A-11P, the following abbreviations mean: FE, Foregut endoderm; OFT, outflow tract; RV, right ventricle; LV, left ventricle.

The observed decreased expression of Isl1 might be reflective of a requirement for β-catenin for Isl1 expression, or reflect a selective loss of cells expressing Isl1 in which β-catenin has been deleted. To investigate this issue, co-immunostaining for Isl1 and β-catenin in Isl1-Cre; β-catenin mutants and control littermates was performed (FIGS. 11A-11P). Sections are from Isl1-Cre; β-catenin mutants and littermate controls at E10.5. Controls shown are sections from Isl1-Cre/Isl1+; foxed O-catenin/β-catenin+embryos, but similar results were obtained with littermate controls of all other genotypes. Co-immunostaining was performed with antibodies to Isl1 (green) and β-catenin (red), and sections were counterstained with DAPI (blue) (FIGS. 11A-11P).

Results of this analysis demonstrated that β-catenin was efficiently ablated in regions overlapping with Isl1 expression and in descendents of Isl1-expressing cells, the latter including a majority of cells within the outflow tract and right ventricle. In cells lacking β-catenin protein, Isl1 expression was still evident, demonstrating their survival, but levels of Isl1 protein were reduced within each cell. No decreases in Isl1 protein levels were observed in littermate controls of all other genotypes, including embryos which were heterozygous null for Isl1. These data suggested that decreased Isl1 expression in Isl1-Cre; β-catenin mutants is consequent to regulation of Isl1 expression by β-catenin, in a direct or indirect manner.

Figures 12A, 12B, 12C:
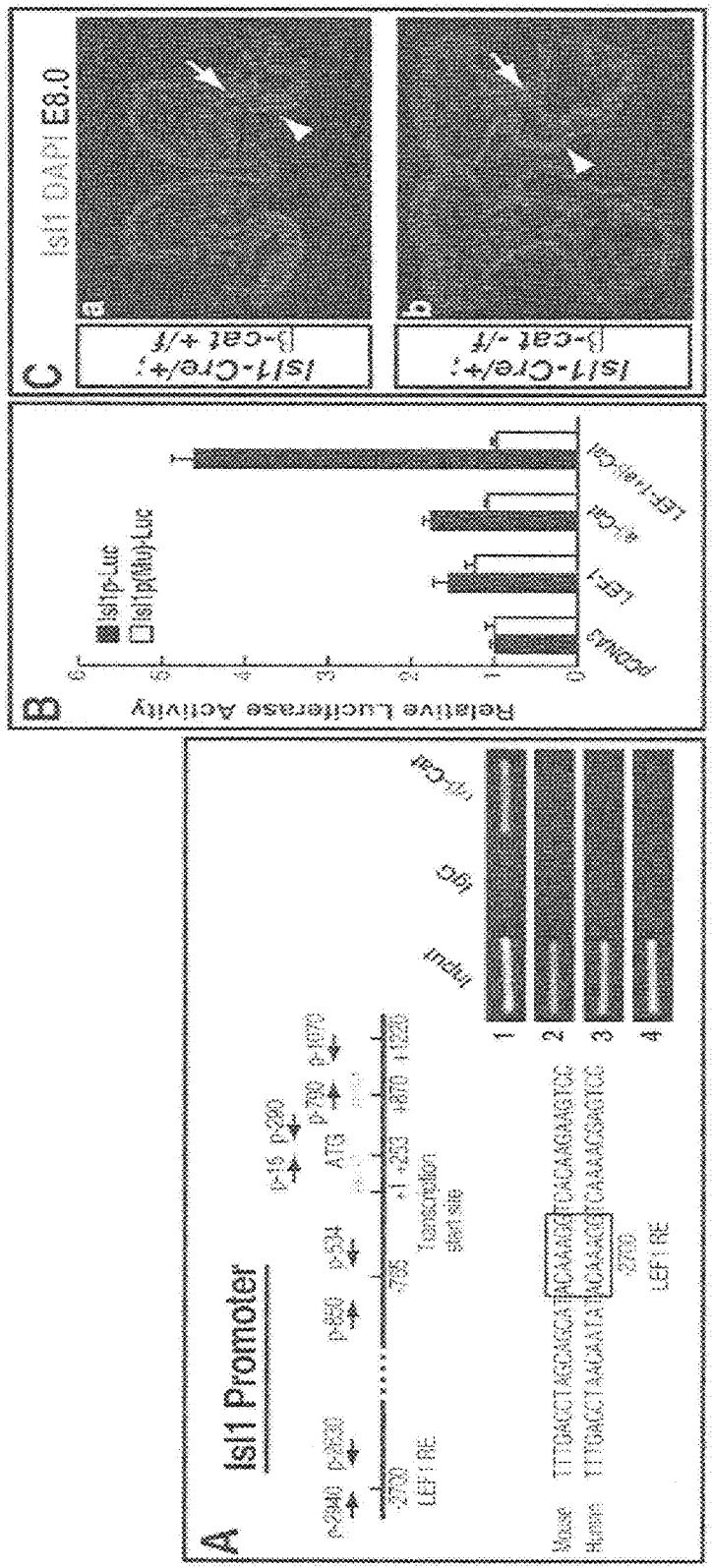
FIGS. 12A-12C are graphical and pictorial diagrams showing that β-catenin acts at early stages of cardiogenesis to directly regulate isl1 expression.

Bioinformatics analysis using standard parameters in rVISTA to examine potential Isl1 promoter regions revealed two evolutionarily conserved LEF1 sites 5' of the ATG start site, or within intron 1 of Isl1 genomic sequences. Chromatin immunoprecipitation (ChIP) analysis performed utilizing extracts from E9.5 embryonic heart and antibodies to β-catenin demonstrated specific binding to the 5' conserved LEF1 response element (FIG. 12A). ChIP assay on extracts from E8.5-9.0 hearts showing in vivo recruitment of β-catenin to the Isl1 5'-promoter with conserved LEF-1 binding sites (Lane 1, primer P-2940, P-2630). ChIP analysis with control primers against distinct promoter regions revealed no recruitment of β-catenin (αβ-Cat, Lanes 2, 3 and 4). No recruitment was observed with IgG control.

To investigate the functional significance of binding, cotransfection assays were performed with a 5 kb Isl1-promoter-Luciferase reporter and expression vectors for LEF-1 and activated β-catenin. HEK293 cells were transiently transfected with Isl1 promoter-luciferase reporter (Isl1--Luc) constructs in combination with either control expression vector, LEF-1 or constitutively active β-catenin (ab-Cat) expression constructs. Isl1p-Luc=wildtype isl1 promoter-Luciferase construct, Islip (Mu)-Luc=isl1 promoter-Luciferase construct with mutated LEF-1 consensus sites. Data obtained from three independent experiments, each performed in triplicate. Data are presented as fold activity over basal promoter activity (relative activity), and are expressed as mean±SD of triplicates from a representative experiment.

Results of these assays demonstrated activation of the isl1-promoter by recruitment of LEF-1 and activated β-catenin (FIG. 12B). Activation was disrupted by mutation of the two conserved LEF-1 binding sites (FIG. 12B), demonstrating that activation by LEF/β-catenin was dependent on the LEF-1 consensus site and that the LEF/β-catenin pathway directly regulates the Isl1 promoter.

Isl1 protein is decreased by E8.0 in Isl1-Cre; β-catenin mutants. Ablation of catenin by Isl1-Cre dictates that β-catenin ablation occurs following expression of Isl1. To investigate whether Isl1 expression was affected at early stages in Isl1-Cre; β-catenin mutants, immunostaining with Isl1 antibody on sections from E8.0 embryos was performed (FIG. 12C). Results of this analysis demonstrated significantly less Isl1 signal both in pharyngeal mesoderm and pharyngeal endoderm in Isl1-Cre; β-catenin mutants relative to control littermates, demonstrating an early requirement for β-catenin. Immunohistochemical analysis demonstrated reduced Isl1 protein levels within Isl1+ cardiovascular progenitors (arrows) and endoderm (arrowheads) in Isl1-Cre; β-catenin mutants when compared to control littermates. Isl1/Nkx2.5/flk1 multipotent progenitors reside in the pharyngeal mesoderm domain at this stage, and Isl1 is reduced in this domain in Isl1-Cre; β-catenin mutants. Immunostaining analysis was performed in parallel on multiple experimental and control samples, and exposure times were the same for all samples.

Figures 13A, 13B, 13C, 13D, 13E, 13F, 13G, 13H:
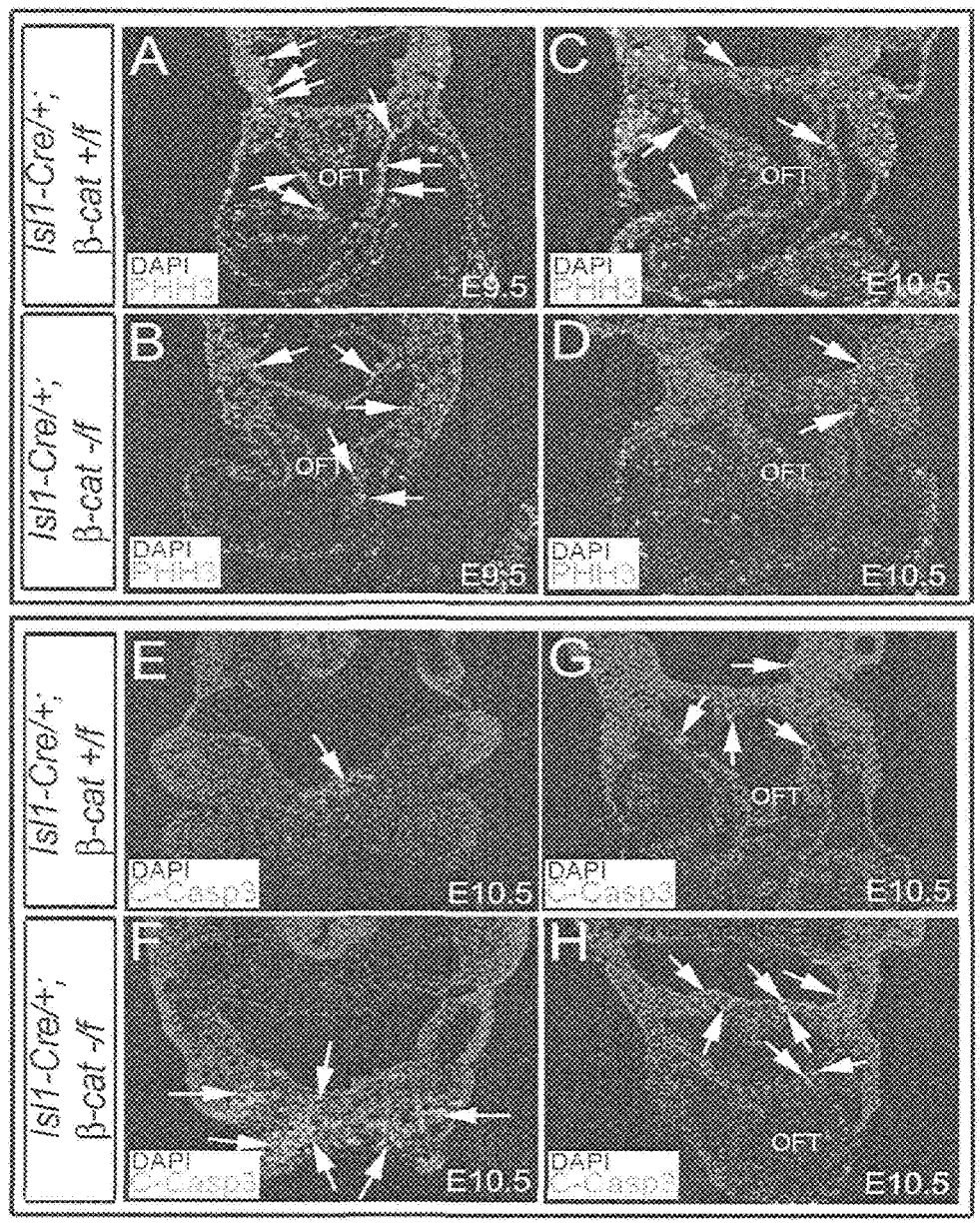
FIGS. 13A-13H are pictorial diagrams showing that β-catenin is required for proliferation and survival of cardiac progenitors.

Proliferation and apoptosis in Isl1-Cre; β-catenin mutants. Smaller branchial arch derivatives, outflow tract and right ventricle in Isl1-Cre; β-catenin mutants suggested that proliferation and/or apoptosis were altered in mutants. To investigate this, immunostaining was performed for phosphorylated histone H3 and cleaved activated caspase 3 to investigate proliferation and apoptosis, respectively. Proliferation was assessed by antibody staining for phosphorylated histone H3 (PHH3). Proliferation rate was significantly decreased in the foregut endoderm and in myocardium of outflow tract in Isl1-Cre; β-catenin mutants. Cleaved Caspase 3 antibody staining showed increased apoptosis in the pharyngeal mesoderm, foregut endoderm and outflow tract at E10.5 in Isl1-Cre; β-catenin mutants relative to control littermates (FIGS. 13G-13I-D. Arrows in FIGS. 13A-13D indicate proliferating cells. Arrows in FIGS. 13E-13H indicate apoptotic cells.

Results of this analysis demonstrated both a reduction in proliferation rate and an increase in apoptosis (FIGS. 13A-13H), At E9.5 (FIGS. 13A, 13B, 13E), proliferation rate in outflow tract myocardium was reduced from 4.6% in wildtype to 2.1% in mutants, and in foregut endoderm was reduced from 3.9% in wildtype to 1.6% in mutants. At E10.5 (FIGS. 13C-13E), the proliferation rate in outflow tract myocardium was reduced from 3.8% in wildtype to 1.0% in mutants, and in foregut endoderm was reduced from 3.1% in wildtype to 1.5% in mutants. At E10.5 (FIGS. 13F-13I), significant increases in apoptotic cells were observed in pharyngeal mesoderm, foregut endoderm and outflow tract, in regions consistent with those similarly affected in Isl1 or hedgehog signaling mutants.

Figures 14A, 14B:
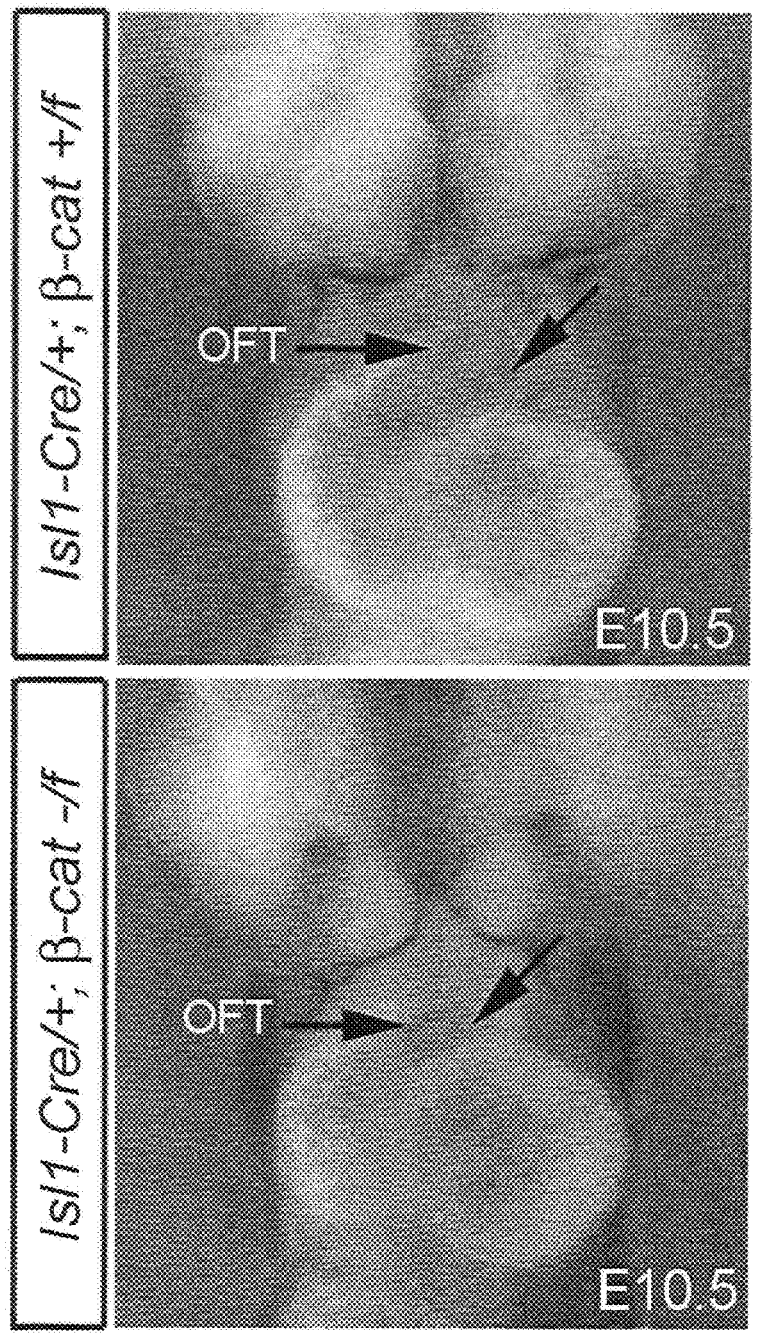
FIGS. 14A and 14B are pictorial diagrams showing that β-catenin is not required for migration of cardiac neural crest cells.

Analysis of cardiac neural crest cells in Isl1-Cre; β-catenin mutants. As cardiac neural crest cells are required for outflow tract septation, Isl1-Cre; β-catenin mutants and littermate controls were examined for expression of the cardiac neural crest marker, PlexinA2. Results demonstrated that PlexinA2 expressing cells were observed in outflow tract of Isl1-Cre; β-catenin mutants, but were less abundant relative to littermate controls (FIGS. 14A and 14B). Whole mount RNA in situ analysis was performed for E10.5 Isl1-Cre; β-catenin mutants and littermate controls utilizing a marker specific for cardiac neural crest cells, PlexinA2. Results demonstrated that PlexinA2 expressing cells were observed in outflow tract of Isl1-Cre; β-catenin mutants, but were less abundant relative to littermate controls (arrows).

Figure 15:
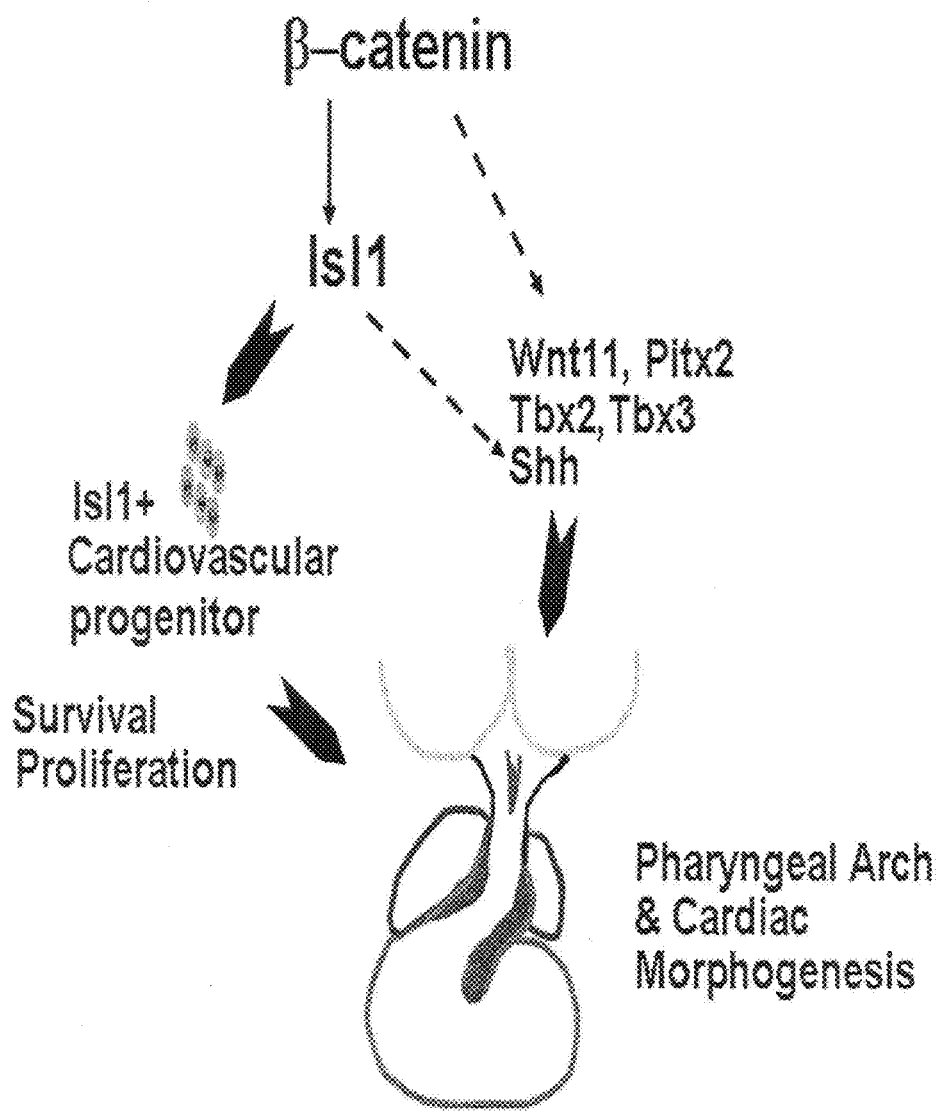
FIG. 15 is a pictorial diagram showing that β-catenin is required for Isl1 expression in cardiovascular progenitors.

FIG. 15 shows that β-catenin is required for Isl1 expression in cardiovascular progenitors. β-catenin directly regulates Isl1 which is required for survival and proliferation of Isl1+ cardiovascular progenitors. β-catenin is upstream of multiple genes which are required for pharyngeal arch and cardiac morphogenesis. Isl1 is upstream of Shh, but β-catenin may also regulate Shh independently of its regulation of isl1. Direct regulation is indicated by solid arrow; direct or indirect regulation is indicated by dotted arrows (FIG. 15).

Although the present process has been described with reference to specific details of certain embodiments thereof in the above examples, it will be understood that modifications and variations are encompassed within the spirit and scope of the invention. Accordingly, the invention is limited only by the following claims.

What is claimed is:

1. A method of identifying a small molecule affecting cardiogenesis, wherein the small molecule is not Tamoxifen, comprising:
   (a) contacting the small molecule with a cell fraction isolated from a transgenic non-human animal having a tamoxifen-dependent Cre-recombinase in the isl1 locus (isl1-mER-Cre-mER) and an Cre reporter with a fluorescent label,
   (b) identifying increased fluorescence from the cell fraction;
   (c) quantifying the expression of isl1+; and (d) identifying an increase or decrease in the expression of isl1+, wherein increased fluorescence from the cell fraction or increased expression of isl1+ is indicative of cardiogenesis, thereby identifying a small molecule which regulates cardiogenesis.

2. The method of claim 1, wherein the non-human animal is a rat or mouse.

3. The method of claim 1, further comprising detecting expression of one or more growth factors selected from the group consisting of BMP4, BMP7, and FGF10.

4. A method of identifying a small molecule which regulates cardiogenesis, wherein the small molecule is not Tamoxifen, comprising:

(a) contacting the small molecule with a cell fraction isolated from a transgenic non-human animal having a tamoxifen-dependent Cre-recombinase in the isl1 locus (isl1-mER-Cre-mER) and an Cre reporter with a fluorescent label;

(b) identifying increased fluorescence from the cell fraction;

(c) quantifying the expression of isl1+; and (d) identifying an increase or decrease in the expression of isl1+, wherein increased fluorescence from the cell fraction or increased expression of isl1+ is indicative of cardiogenesis, thereby identifying a small molecule which regulates cardiogenesis.

5. The method of claim 4, wherein the non-human animal is a rat or mouse.

6. The method of claim 4, further comprising detecting expression of one or more growth factors selected from the group consisting of BMP4, BMP7, and FGF10.

* * * * *

```
                            SEQUENCE LISTING

<160> NUMBER OF SEQ ID NOS: 12

<210> SEQ ID NO 1
<211> LENGTH: 21
<212> TYPE: DNA
<213> ORGANISM: Artificial sequence
<220> FEATURE:
<223> OTHER INFORMATION: Primer

<400> SEQUENCE: 1
gcgccaggaa ctgtgctcca a                                          21

<210> SEQ ID NO 2
<211> LENGTH: 24
<212> TYPE: DNA
<213> ORGANISM: Artificial sequence
<220> FEATURE:
<223> OTHER INFORMATION: Primer

<400> SEQUENCE: 2
aggggcgacc tcttgtgttc aatg                                       24

<210> SEQ ID NO 3
<211> LENGTH: 24
<212> TYPE: DNA
<213> ORGANISM: Artificial sequence
<220> FEATURE:
<223> OTHER INFORMATION: Primer

<400> SEQUENCE: 3
gaacaggaga cctcacgggt cggg                                       24

<210> SEQ ID NO 4
<211> LENGTH: 24
<212> TYPE: DNA
<213> ORGANISM: Artificial sequence
<220> FEATURE:
<223> OTHER INFORMATION: Primer

<400> SEQUENCE: 4
ctagcagcgc gctacgcgtt aggg                                       24

<210> SEQ ID NO 5
<211> LENGTH: 24
<212> TYPE: DNA
<213> ORGANISM: Artificial sequence
<220> FEATURE:
<223> OTHER INFORMATION: Primer

<400> SEQUENCE: 5
gaagagaggt gccccgagcc gtgc                                       24

<210> SEQ ID NO 6
<211> LENGTH: 24
<212> TYPE: DNA
<213> ORGANISM: Artificial sequence
<220> FEATURE:
<223> OTHER INFORMATION: Primer

<400> SEQUENCE: 6
tttggtggat cgcccatgtc tccc                                       24
```

```
<210> SEQ ID NO 7
<211> LENGTH: 24
<212> TYPE: DNA
<213> ORGANISM: Artificial sequence
<220> FEATURE:
<223> OTHER INFORMATION: Primer

<400> SEQUENCE: 7
cccgcgtgct attgaagaac gtgc                                              24

<210> SEQ ID NO 8
<211> LENGTH: 24
<212> TYPE: DNA
<213> ORGANISM: Artificial sequence
<220> FEATURE:
<223> OTHER INFORMATION: Primer

<400> SEQUENCE: 8
ttgggatggt aattggagtg tgcc                                              24

<210> SEQ ID NO 9
<211> LENGTH: 28
<212> TYPE: DNA
<213> ORGANISM: Artificial sequence
<220> FEATURE:
<223> OTHER INFORMATION: Primer

<400> SEQUENCE: 9
gatggtaccc tcaactaaat gaggctac                                          28

<210> SEQ ID NO 10
<211> LENGTH: 29
<212> TYPE: DNA
<213> ORGANISM: Artificial sequence
<220> FEATURE:
<223> OTHER INFORMATION: Primer

<400> SEQUENCE: 10
attgtcgact tgtaagaggg agtaatgtc                                         29

<210> SEQ ID NO 11
<211> LENGTH: 36
<212> TYPE: DNA
<213> ORGANISM: Mouse

<400> SEQUENCE: 11
tttgacctag cagcatacaa aggtcacaag aagtcc                                 36

<210> SEQ ID NO 12
<211> LENGTH: 36
<212> TYPE: DNA
<213> ORGANISM: Homo sapiens

<400> SEQUENCE: 12
tttgacctaa caatatacaa aggtcaaaac gagtcc                                 36
```